(12) United States Patent
Rosenbluth et al.

(10) Patent No.: US 10,709,471 B2
(45) Date of Patent: Jul. 14, 2020

(54) METHODS AND APPARATUS FOR TREATING EMBOLISM

(71) Applicant: Inari Medical, Inc., Irvine, CA (US)

(72) Inventors: Robert F. Rosenbluth, Laguna Niguel, CA (US); Brian J. Cox, Laguna Niguel, CA (US); Paul Lubock, Monarch Beach, CA (US); Richard Quick, Mission Viejo, CA (US)

(73) Assignee: Inari Medical, Inc., Irvine, CA (US)

( * ) Notice: Subject to any disclaimer, the term of this patent is extended or adjusted under 35 U.S.C. 154(b) by 280 days.

(21) Appl. No.: 15/949,350

(22) Filed: Apr. 10, 2018

(65) Prior Publication Data

US 2018/0296240 A1    Oct. 18, 2018

Related U.S. Application Data

(63) Continuation of application No. 14/646,358, filed as application No. PCT/US2013/071101 on Nov. 20, (Continued)

(51) Int. Cl.
*A61B 17/3207* (2006.01)
*A61B 17/221* (2006.01)
(Continued)

(52) U.S. Cl.
CPC .... *A61B 17/320725* (2013.01); *A61B 17/221* (2013.01); *A61B 17/22032* (2013.01); (Continued)

(58) Field of Classification Search
CPC .. A61M 2025/0024; A61M 2025/0035; A61M 25/0067; A61M 25/0068;
(Continued)

(56) References Cited

U.S. PATENT DOCUMENTS

| 2,846,179 A | 8/1958 | Monckton |
| 3,088,363 A | 5/1963 | Sparks |

(Continued)

FOREIGN PATENT DOCUMENTS

| DE | 102017004383 | 7/2018 |
| JP | 6190049 | 7/1994 |

(Continued)

OTHER PUBLICATIONS

International Search Report and Written Opinion for International App. No. PCT/US2018/055780, Date of Filing: Oct. 13, 2018, Applicant: Inceptus Medical LLC., dated Jan. 22, 2019, 8 pages.
(Continued)

*Primary Examiner* — Wade Miles
(74) *Attorney, Agent, or Firm* — Perkins Coie LLP

(57) ABSTRACT

A method and apparatus for treating a clot in the blood vessel of a patient, and particularly the treatment of a pulmonary embolism is disclosed. The treatment includes restoring flow through the clot followed by clot removal, either partially or substantially completely. The clot treatment device is expandable into the blood vessel and may contain radial extensions that assist in restoring flow as well as in removing clot material.

16 Claims, 21 Drawing Sheets

Related U.S. Application Data 2013, now Pat. No. 10,004,531, which is a continuation-in-part of application No. 13/843,742, filed on Mar. 15, 2013, now Pat. No. 8,784,434.

(60) Provisional application No. 61/728,775, filed on Nov. 20, 2012, provisional application No. 61/750,277, filed on Jan. 8, 2013.

(51) Int. Cl.
*A61B 17/22* (2006.01)
*A61B 17/00* (2006.01)
*A61M 39/04* (2006.01)

(52) U.S. Cl.
CPC .............. *A61B 17/32075* (2013.01); *A61B 2017/00809* (2013.01); *A61B 2017/00862* (2013.01); *A61B 2017/00867* (2013.01); *A61B 2017/22034* (2013.01); *A61B 2017/22038* (2013.01); *A61B 2017/22081* (2013.01); *A61B 2017/22094* (2013.01); *A61B 2017/320716* (2013.01); *A61B 2217/005* (2013.01); *A61M 39/04* (2013.01)

(58) Field of Classification Search
CPC ...... A61M 25/0069; A61M 2025/0073; A61M 25/0074; A61F 2002/9528; A61F 2002/9534; A61F 2002/011; A61B 2017/22035; A61B 17/221; A61B 2017/2212; A61B 2017/2215; A61B 2017/2217; A61B 17/22031; A61B 2017/22034; A61B 17/3207; A61B 2017/320716; A61B 17/320725; A61B 2017/320741; A61B 17/32056; A61B 17/32075; A61B 17/320758; A61B 2017/320766; A61B 2017/320775
See application file for complete search history.

(56) References Cited

U.S. PATENT DOCUMENTS

| | | | |
|---|---|---|---|
| 3,435,826 A | 4/1969 | Fogarty |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,287,808 A | 9/1981 | Leonard et al. |
| 4,393,872 A | 7/1983 | Reznik et al. |
| 4,523,738 A | 6/1985 | Raftis et al. |
| 4,551,862 A | 11/1985 | Haber |
| 4,650,466 A | 3/1987 | Luther |
| 4,873,978 A | 10/1989 | Ginsburg |
| 4,883,458 A | 11/1989 | Shiber |
| 4,890,611 A | 1/1990 | Monfort et al. |
| 4,978,341 A | 12/1990 | Niederhauser |
| 5,011,488 A | 4/1991 | Ginsburg |
| 5,059,178 A | 10/1991 | Ya |
| 5,102,415 A | 4/1992 | Guenther et al. |
| 5,129,910 A | 7/1992 | Phan et al. |
| 5,192,286 A | 3/1993 | Phan et al. |
| 5,192,290 A | 3/1993 | Hilal |
| 5,360,417 A | 11/1994 | Gravener et al. |
| 5,370,653 A | 12/1994 | Cragg |
| 5,476,450 A | 12/1995 | Ruggio |
| 5,490,859 A | 2/1996 | Mische et al. |
| 5,591,137 A | 1/1997 | Stevens |
| 5,746,758 A | 5/1998 | Nordgren et al. |
| 5,749,858 A | 5/1998 | Cramer |
| 5,766,191 A | 6/1998 | Trerotola |
| 5,782,817 A | 7/1998 | Franzel et al. |
| 5,827,304 A | 10/1998 | Hart |
| 5,868,708 A | 2/1999 | Hart et al. |
| 5,873,866 A | 2/1999 | Kondo et al. |
| 5,873,882 A | 2/1999 | Straub et al. |
| 5,876,414 A | 3/1999 | Straub |
| 5,882,329 A | 3/1999 | Patterson et al. |
| 5,972,019 A | 10/1999 | Engelson et al. |
| 5,974,938 A | 11/1999 | Lloyd |
| 5,993,483 A | 11/1999 | Gianotti |
| 6,066,149 A | 5/2000 | Samson et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,254,571 B1 | 7/2001 | Hart |
| 6,258,115 B1 | 7/2001 | Dubrul |
| 6,306,163 B1 | 10/2001 | Fitz |
| 6,350,271 B1 | 2/2002 | Kurz et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,413,235 B1 | 7/2002 | Parodi |
| 6,423,032 B2 | 7/2002 | Parodi |
| 6,440,148 B1 | 8/2002 | Shiber |
| 6,454,741 B1 | 9/2002 | Muni et al. |
| 6,454,775 B1 | 9/2002 | Demarais et al. |
| 6,458,103 B1 | 10/2002 | Albert et al. |
| 6,458,139 B1 | 10/2002 | Palmer et al. |
| 6,511,492 B1 | 1/2003 | Rosenbluth et al. |
| 6,514,273 B1 | 2/2003 | Voss et al. |
| 6,530,935 B2 | 3/2003 | Wensel et al. |
| 6,530,939 B1 | 3/2003 | Hopkins et al. |
| 6,544,279 B1 | 4/2003 | Hopkins et al. |
| 6,551,342 B1 | 4/2003 | Shen et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,605,074 B2 | 8/2003 | Zadno-Azizi et al. |
| 6,605,102 B1 | 8/2003 | Mazzocchi et al. |
| 6,623,460 B1 | 9/2003 | Heck |
| 6,635,070 B2 | 10/2003 | Leeflang et al. |
| 6,645,222 B1 | 11/2003 | Parodi et al. |
| 6,660,013 B2 | 12/2003 | Rabiner et al. |
| 6,663,650 B2 | 12/2003 | Sepetka et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,755,847 B2 | 6/2004 | Eskuri |
| 6,767,353 B1 | 7/2004 | Shiber |
| 6,800,080 B1 | 10/2004 | Bates |
| 6,824,553 B1 | 11/2004 | Gene et al. |
| 6,939,361 B1 | 9/2005 | Kleshinski |
| 6,960,222 B2 | 11/2005 | Vo et al. |
| 7,004,954 B1 | 2/2006 | Voss et al. |
| 7,036,707 B2 | 5/2006 | Aota et al. |
| 7,041,084 B2 | 5/2006 | Fojtik |
| 7,052,500 B2 | 5/2006 | Bashiri et al. |
| 7,056,328 B2 | 6/2006 | Arnott |
| 7,069,835 B2 | 7/2006 | Nishri et al. |
| 7,094,249 B1 | 8/2006 | Thomas et al. |
| 7,179,273 B1 | 2/2007 | Palmer et al. |
| 7,220,269 B1 | 5/2007 | Ansel et al. |
| 7,232,432 B2 | 6/2007 | Fulton, III et al. |
| 7,244,243 B2 | 7/2007 | Lary |
| 7,285,126 B2 | 10/2007 | Sepetka et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,534,234 B2 | 5/2009 | Fojtik |
| 7,578,830 B2 | 8/2009 | Kusleika et al. |
| 7,621,870 B2 | 11/2009 | Berrada et al. |
| 7,674,247 B2 | 3/2010 | Fojtik |
| 7,691,121 B2 | 4/2010 | Rosenbluth et al. |
| 7,695,458 B2 | 4/2010 | Belley et al. |
| 7,763,010 B2 | 7/2010 | Evans et al. |
| 7,766,934 B2 | 8/2010 | Pal et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |

(56) References Cited

U.S. PATENT DOCUMENTS

| | | |
|---|---|---|
| 7,976,511 B2 | 7/2011 | Fojtik |
| 7,993,302 B2 | 8/2011 | Hebert et al. |
| 7,993,363 B2 | 8/2011 | Demond et al. |
| 8,043,313 B2 | 10/2011 | Krolik et al. |
| 8,052,640 B2 | 11/2011 | Fiorella et al. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,088,140 B2 | 1/2012 | Ferrera et al. |
| 8,100,935 B2 | 1/2012 | Rosenbluth et al. |
| 8,109,962 B2 | 2/2012 | Pal |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fojtik |
| RE43,902 E | 1/2013 | Hopkins et al. |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,486,105 B2 | 7/2013 | Demond et al. |
| 8,491,539 B2 | 7/2013 | Fojtik |
| 8,512,352 B2 | 8/2013 | Martin |
| 8,535,334 B2 | 9/2013 | Martin |
| 8,545,526 B2 | 10/2013 | Martin et al. |
| 8,568,432 B2 | 10/2013 | Straub |
| 8,574,262 B2 | 11/2013 | Ferrera et al. |
| 8,579,915 B2 | 11/2013 | French et al. |
| 8,585,713 B2 | 11/2013 | Ferrera et al. |
| 8,696,622 B2 | 4/2014 | Fiorella et al. |
| 8,771,289 B2 | 7/2014 | Mohiuddin et al. |
| 8,777,893 B2 | 7/2014 | Malewicz |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,345 B2 | 8/2014 | Grandfield et al. |
| 8,801,748 B2 | 8/2014 | Martin |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,845,621 B2 | 9/2014 | Fojtik |
| 8,852,205 B2 | 10/2014 | Brady et al. |
| 8,852,226 B2 | 10/2014 | Gilson et al. |
| 8,932,319 B2 | 1/2015 | Martin et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 8,992,504 B2 | 3/2015 | Castella et al. |
| 9,005,172 B2 | 4/2015 | Chung |
| 9,101,382 B2 | 8/2015 | Krolik et al. |
| 9,149,609 B2 | 10/2015 | Ansel et al. |
| 9,161,766 B2 | 10/2015 | Slee et al. |
| 9,204,887 B2 | 12/2015 | Cully et al. |
| 9,259,237 B2 | 2/2016 | Quick et al. |
| 9,283,066 B2 | 3/2016 | Hopkins et al. |
| 9,408,620 B2 | 8/2016 | Rosenbluth |
| 9,439,664 B2 | 9/2016 | Sos |
| 9,439,751 B2 | 9/2016 | White et al. |
| 9,456,834 B2 | 10/2016 | Folk |
| 9,463,036 B2 | 10/2016 | Brady et al. |
| 9,526,864 B2 | 12/2016 | Quick |
| 9,526,865 B2 | 12/2016 | Quick |
| 9,566,424 B2 | 2/2017 | Pessin |
| 9,616,213 B2 | 4/2017 | Furnish et al. |
| 9,700,332 B2 | 7/2017 | Marchand et al. |
| 9,717,519 B2 | 8/2017 | Rosenbluth et al. |
| 9,757,137 B2 | 9/2017 | Krolik et al. |
| 9,844,387 B2 | 12/2017 | Marchand et al. |
| 10,004,531 B2 | 6/2018 | Rosenbluth et al. |
| 10,045,790 B2 | 8/2018 | Cox et al. |
| 10,098,651 B2 | 10/2018 | Marchand et al. |
| 1,023,840 A1 | 3/2019 | Cox et al. |
| 10,335,186 B2 | 7/2019 | Rosenbluth et al. |
| 10,342,571 B2 | 7/2019 | Marchand et al. |
| 10,349,960 B2 | 7/2019 | Quick |
| 2001/0004699 A1 | 6/2001 | Gittings et al. |
| 2001/0041909 A1 | 11/2001 | Tsugita et al. |
| 2001/0051810 A1 | 12/2001 | Dubrul et al. |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0156457 A1 | 10/2002 | Fisher |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135230 A1 | 7/2003 | Massey et al. |
| 2003/0153973 A1 | 8/2003 | Soun et al. |
| 2004/0039412 A1 | 2/2004 | Isshiki et al. |
| 2004/0073243 A1 | 4/2004 | Sepetka et al. |
| 2005/0038468 A1 | 2/2005 | Panetta et al. |
| 2005/0119668 A1 | 6/2005 | Teague et al. |
| 2005/0283186 A1 | 12/2005 | Berrada et al. |
| 2006/0047286 A1 | 3/2006 | West |
| 2006/0100662 A1 | 5/2006 | Daniel et al. |
| 2006/0247500 A1 | 11/2006 | Voegele et al. |
| 2006/0253145 A1 | 11/2006 | Lucas |
| 2006/0282111 A1 | 12/2006 | Morsi |
| 2007/0112374 A1 | 5/2007 | Paul, Jr. et al. |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0255252 A1 | 11/2007 | Mehta |
| 2008/0015541 A1 | 1/2008 | Rosenbluth et al. |
| 2008/0088055 A1 | 4/2008 | Ross |
| 2008/0157017 A1 | 7/2008 | Macatangay et al. |
| 2008/0167678 A1 | 7/2008 | Morsi |
| 2008/0228209 A1 | 9/2008 | DeMello et al. |
| 2008/0234722 A1 | 9/2008 | Bonnette et al. |
| 2008/0269798 A1 | 10/2008 | Ramzipoor et al. |
| 2008/0300466 A1 | 12/2008 | Gresham |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0281525 A1 | 11/2009 | Harding et al. |
| 2009/0292307 A1 | 11/2009 | Razack |
| 2010/0087850 A1 | 4/2010 | Razack |
| 2010/0114113 A1 | 5/2010 | Dubrul et al. |
| 2010/0121312 A1 | 5/2010 | Gielenz et al. |
| 2010/0204712 A1 | 8/2010 | Mallaby |
| 2010/0249815 A1 | 9/2010 | Jantzen et al. |
| 2010/0318178 A1 | 12/2010 | Rapaport et al. |
| 2011/0054405 A1 | 3/2011 | Whiting et al. |
| 2011/0060212 A1 | 3/2011 | Slee et al. |
| 2011/0144592 A1 | 6/2011 | Wong et al. |
| 2011/0152993 A1 | 6/2011 | Marchand et al. |
| 2011/0190806 A1 | 8/2011 | Wittens |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0251629 A1 | 10/2011 | Galdonik et al. |
| 2011/0264133 A1 | 10/2011 | Hanlon et al. |
| 2011/0319917 A1 | 12/2011 | David et al. |
| 2012/0089216 A1 | 4/2012 | Rapaport et al. |
| 2012/0101480 A1 | 4/2012 | Ingle et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0232655 A1 | 9/2012 | Lorrison et al. |
| 2012/0271231 A1 | 10/2012 | Agrawal |

(56) References Cited

U.S. PATENT DOCUMENTS

| | | |
|---|---|---|
| 2012/0310166 A1 | 12/2012 | Huff |
| 2013/0092012 A1 | 4/2013 | Marchand et al. |
| 2013/0184703 A1 | 7/2013 | Brice et al. |
| 2014/0005713 A1 | 1/2014 | Bowman |
| 2014/0025048 A1 | 1/2014 | Ward |
| 2015/0018860 A1 | 1/2015 | Quick et al. |
| 2015/0133990 A1 | 5/2015 | Davidson |
| 2015/0196744 A1 | 7/2015 | Aboytes |
| 2015/0238207 A1 | 8/2015 | Cox et al. |
| 2015/0265299 A1 | 9/2015 | Cooper et al. |
| 2015/0305756 A1 | 10/2015 | Rosenbluth et al. |
| 2015/0305859 A1 | 10/2015 | Eller |
| 2015/0352325 A1 | 12/2015 | Quick |
| 2015/0360001 A1 | 12/2015 | Quick |
| 2015/0374391 A1 | 12/2015 | Quick et al. |
| 2016/0113666 A1 | 4/2016 | Quick et al. |
| 2016/0143721 A1 | 5/2016 | Rosenbluth et al. |
| 2016/0262790 A1 | 9/2016 | Rosenbluth et al. |
| 2016/0277276 A1 | 10/2016 | Cox et al. |
| 2017/0037548 A1 | 2/2017 | Lee |
| 2017/0058623 A1 | 3/2017 | Jaffrey et al. |
| 2017/0105745 A1 | 4/2017 | Rosenbluth et al. |
| 2017/0112514 A1 | 4/2017 | Marchand et al. |
| 2017/0189041 A1 | 7/2017 | Cox et al. |
| 2017/0233908 A1 | 8/2017 | Kroczynski et al. |
| 2017/0265878 A1 | 9/2017 | Marchand et al. |
| 2017/0325839 A1 | 11/2017 | Rosenbluth et al. |
| 2018/0092652 A1 | 4/2018 | Marchand et al. |
| 2018/0105963 A1 | 4/2018 | Quick |
| 2018/0193043 A1 | 7/2018 | Marchand et al. |
| 2018/0256178 A1 | 9/2018 | Cox et al. |
| 2018/0344339 A1 | 12/2018 | Cox et al. |
| 2018/0361116 A1 | 12/2018 | Quick et al. |
| 2019/0046219 A1 | 2/2019 | Marchand et al. |
| 2019/0070401 A1 | 3/2019 | Merritt et al. |
| 2019/0150959 A1 | 5/2019 | Cox et al. |
| 2019/0231373 A1 | 8/2019 | Quick |

FOREIGN PATENT DOCUMENTS

| | | | |
|---|---|---|---|
| JP | 2001522631 | | 5/1999 |
| JP | 2004097807 | A | 4/2004 |
| JP | 2005230132 | A | 9/2005 |
| JP | 2005323702 | A | 11/2005 |
| JP | 2006094876 | A | 4/2006 |
| JP | 2011526820 | | 1/2010 |
| WO | WO-1997017889 | A1 | 5/1997 |
| WO | WO-1999044542 | | 9/1999 |
| WO | WO-2000053120 | | 9/2000 |
| WO | WO-2005046736 | | 5/2005 |
| WO | WO-2006110186 | | 10/2006 |
| WO | WO-2007092820 | A2 | 8/2007 |
| WO | WO-2009155571 | A1 | 12/2009 |
| WO | WO2010002549 | | 1/2010 |
| WO | WO-2010010545 | A1 | 1/2010 |
| WO | WO-2010023671 | A2 | 3/2010 |
| WO | WO-2010049121 | A2 | 5/2010 |
| WO | WO-2010102307 | A1 | 9/2010 |
| WO | WO-2011054531 | A2 | 5/2011 |
| WO | WO-2012009675 | A2 | 1/2012 |
| WO | WO-2012011097 | | 4/2012 |
| WO | WO-2012/065748 | A1 | 5/2012 |
| WO | WO2012120490 | | 9/2012 |
| WO | WO-2014047650 | A1 | 3/2014 |
| WO | WO-2014081892 | A1 | 5/2014 |
| WO | WO-2015006782 | A1 | 1/2015 |
| WO | WO-2015061365 | A1 | 4/2015 |
| WO | WO2015191646 | | 12/2015 |
| WO | WO2017024258 | | 2/2017 |
| WO | WO2017070702 | | 4/2017 |
| WO | WO2017106877 | | 6/2017 |
| WO | WO2018080590 | | 5/2018 |
| WO | WO2019050765 | | 3/2019 |
| WO | WO2019075444 | | 4/2019 |

OTHER PUBLICATIONS

European Patent Application No. 13838945.7, Extended European Search Report, 9 pages, dated Apr. 15, 2016.

Gibbs, et al., "Temporary Stent as a bail-out device during percutaneous transluminal coronary angioplasty: preliminary clinical experience," British Heart Journal, 1994, 71:372-377,Oct. 12, 1993 6 pgs.

Goldhaber, S. et al. "Percutaneous Mechanical Thrombectomy for Acute Pulmonary Embolism—A Double-Edged Sword", American College of CHEST Physicians, Aug. 2007: 132:2, 363-372.

Goldhaber, S., "Advanced treatment strategies for acute pulmonary embolism, including thrombolysis and embolectomy", Journal of Thrombosis and Haemostasis, 2009: 7 (Suppl. 1): 322-327.

Gupta, S. et al., "Acute Pulmonary Embolism Advances in Treatment," JAPI, Association of Physicians India, Mar. 2008, vol. 56, 185-191.

International Search Report and Written Opinion for International App. No. PCT/US13/61470, dated Jan. 17, 2014, 7 pages.

International Search Report and Written Opinion for International App. No. PCT/US2014/046567, dated Nov. 3, 2014, 13 pages.

International Search Report and Written Opinion for International App. No. PCT/US2014/061645, dated Jan. 23, 2015, 15 pages.

International Search Report and Written Opinion for International App. No. PCT/US2015/034987, dated Jun. 9, 2015, 12 pages.

International Search Report and Written Opinion for International Application No. PCT/US2015/034987, dated Sep. 17, 2015, 12 pages.

International Search Report for International App. No. PCT/US13/71101, dated Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33; 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", CardiologyRounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Notice of Allowance for U.S. Appl. No. 13/843,742, dated Mar. 12, 2014, 13 pages.

Notice of Allowance for U.S. Appl. No. 14/288,778, dated Dec. 23, 2014, 12 pages.

(56) References Cited

OTHER PUBLICATIONS

Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol 27-254-258, 2004, 5 pgs.
Turk et al., "ADAPT FAST study: a direct aspiration first pass technique for acute stroke thrombectomy." J NeuroIntervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Raiology*, Oct. 2006, 41, 729-734.
International Search Report and Written Opinion for International App. No. PCT/US2015/034987 filed Jun. 9, 2015, Applicant: Inceptus Medical, LLC, dated Sep. 17, 2015, 12 pages.
English translation of Japanese Office Action received for JP Application No. 2016-564210, Applicant: Inceptus Medical, LLC, dated Sep. 4, 2017, 4 pages.
Australian Exam Report received for AU Application No. 2015274704, Applicant: Inceptus Medical, LLC, dated Sep. 7, 2017, 3 pages.
European Search Report received for EP Application No. 15805810.7, Applicant: Inceptus Medical, LLC, dated Sep. 4, 2017, 6 pages.
International Search Report and Written Opinion for International App. No. PCT/US2016/067628 filed Dec. 19, 2016, Applicant: Inari Medical, Inc, dated Apr. 10, 2017, 11 pages.
International Search Report and Written Opinion for International App. No. PCT/US2017/029696, Date of Filing: Apr. 26, 2017, Applicant: Inari Medical, Inc, dated Sep. 15, 2017, 19 pages.
International Search Report and Written Opinion for International App. No. PCT/US2016/058536, Date of Filing: Oct. 24, 2016, Applicant: Inari Medical, Inc, dated Mar. 13, 2017, 14 pages.
European Search Report for European Application No. 16876941.2, Date of Filing: Dec. 19, 2016, Applicant: Inari Medical, Inc., dated Jul. 18, 2019, 7 pages.
Extended European Search Report for European Application No. 16858462.1, Date of Filing: Oct. 24, 2016, Applicant: Inari Medical, Inc., dated Jun. 3, 2019, 10 pages.
European First Office Action received for EP Application No. 13838945.7, Applicant: Inari Medical, Inc., dated Oct. 26, 2018, 7 pages.
International Search Report and Written Opinion for International App. No. PCT/US2018/048786, Date of Filing: Aug. 30, 2018, Applicant: Inari Medical, Inc., dated Dec. 13, 2018, 12 pages.

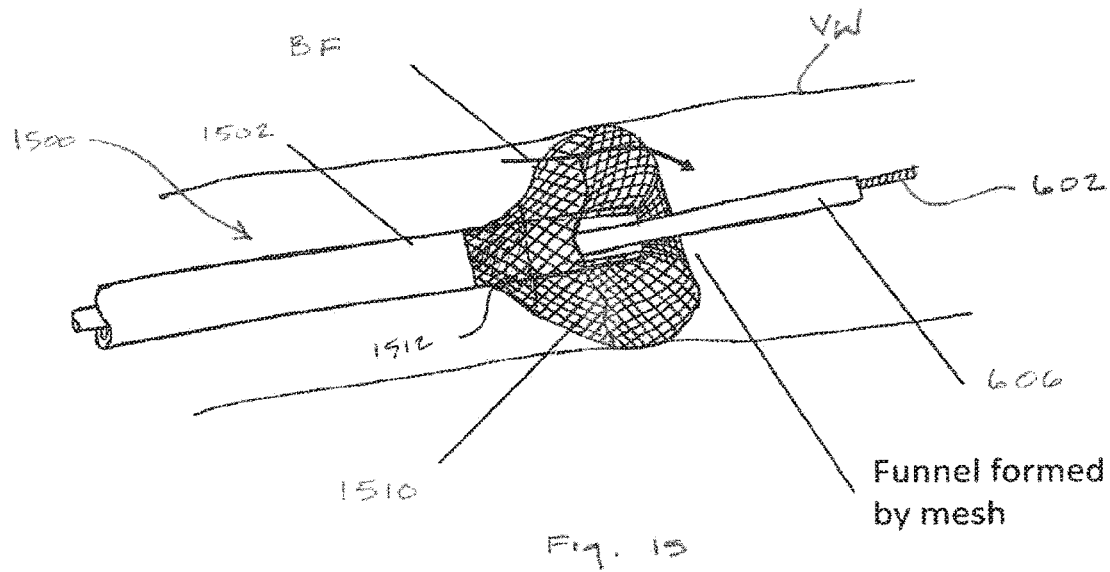
Fig. 15
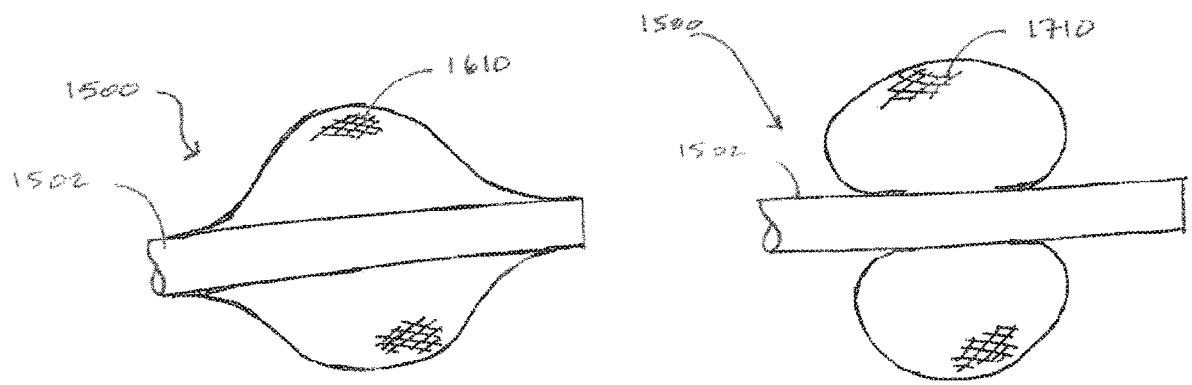
Fig. 16
Fig. 17

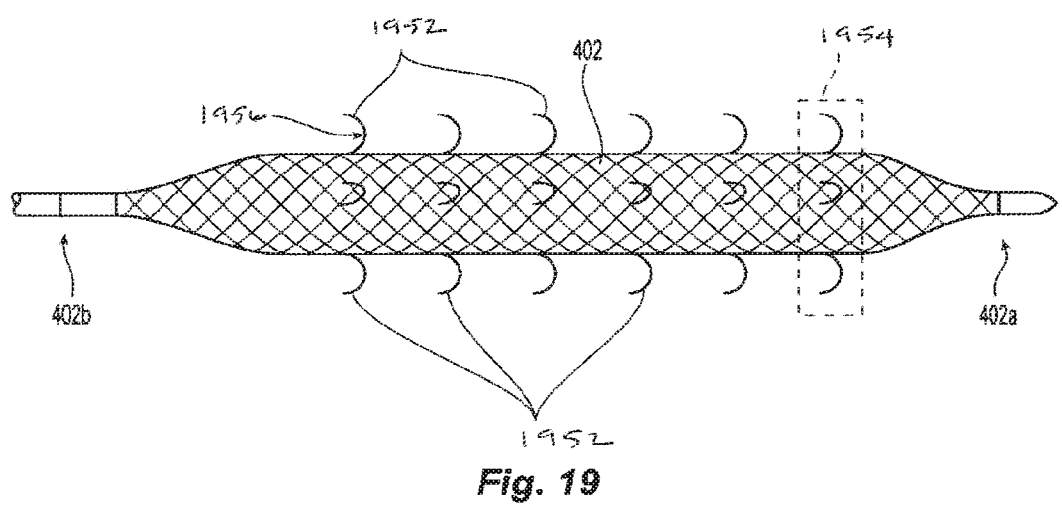
*Fig. 19*
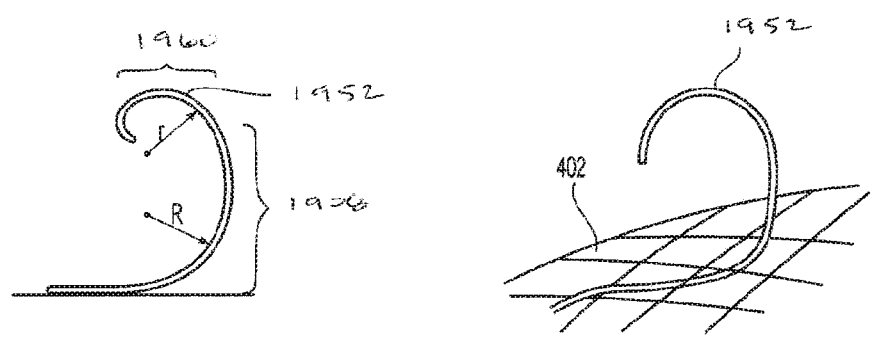
*Fig. 20*     *Fig. 21*

METHODS AND APPARATUS FOR TREATING EMBOLISM

CROSS-REFERENCE TO RELATED APPLICATION(S)

This application is a continuation of U.S. patent application Ser. No. 14/646,358, filed on May 20, 2015 and entitled Methods and Apparatus for Treating Embolism, which is a 371 U.S. national filing of PCT/US2013/071101, filed on Nov. 20, 2013 and entitled Methods and Apparatus for Treating Embolism, which is a continuation-in-part of U.S. patent application Ser. No. 13/843,742, filed on Mar. 15, 2013, now issued as U.S. Pat. No. 8,784,434 and entitled Methods and Apparatus for Treating Embolism, which claims priority to U.S. Provisional Application Ser. No. 61/750,277 filed Jan. 8, 2013 entitled Devices and Methods for Treatment of Vascular Occlusion and U.S. Provisional Application Ser. No. 61/728,775 filed Nov. 20, 2012 entitled Devices and Methods for Treatment of Vascular Occlusion, all of which are hereby incorporated herein by reference in their entireties.

TECHNICAL FIELD

This invention relates to the apparatus and methods of endovascular treatment of blood clots obstructing passageways in the circulatory system and particularly the endovascular treatment of pulmonary embolism.

BACKGROUND

Thromboembolism is the formation in a blood vessel of a clot (thrombus) that breaks loose (embolizes) and is carried by the blood stream to another location in the circulatory system resulting in a clot or obstruction at that new location. For example, a clot may embolize and plug a vessel in the lungs (pulmonary embolism), the brain (stroke), the gastrointestinal tract, the kidneys, or the legs. Thromboembolism is a significant cause of morbidity (disease) and mortality (death), especially in adults. A thromboembolism can be sudden and massive or it may be small and multiple. A thromboembolism can be any size and a thromboembolic event can happen at any time.

When a thrombus forms in the venous circulation of the body it often embolizes to the lungs. Such a thrombus typically embolizes from the veins of the legs, pelvis, or inferior vena cava and travels to the right heart cavities and then into the pulmonary arteries thus resulting in a pulmonary embolism.

A pulmonary embolism results in right heart failure and decreased blood flow through the lungs with subsequent decreased oxygenation of the lungs, heart and the rest of the body. More specifically, when such a thrombus enters the pulmonary arteries, obstruction and spasm of the different arteries of the lung occurs which further decreases blood flow and gaseous exchange through the lung tissue resulting in pulmonary edema. All of these factors decrease the oxygen in the blood in the left heart. As a result, the oxygenated blood supplied by the coronary arteries to the musculature of both the left and right heart is insufficient for proper contractions of the muscle which further decreases the entire oxygenated blood flow to the rest of the body. This often leads to heart dysfunction and specifically right ventricle dysfunction.

This condition is relatively common and has many causes. Some of the more common causes are prolonged inactivity such as bed rest, extended sitting (e.g., lengthy aircraft travel), dehydration, extensive surgery or protracted disease. Almost all of these causes are characterized by the blood of the inferior peripheral major circulatory system coagulating to varying degrees and resulting in permanent drainage problems.

There exist a number of approaches to treating thromboembolism and particularly pulmonary embolism. Some of those approaches include the use of anticoagulants, thrombolytics and endovascular attempts at removal of the emboli from the pulmonary artery. The endovascular attempts often rely on catheterization of the affected vessels and application of chemical or mechanical agents or both to disintegrate the clot. Invasive surgical intervention in which the emboli is removed by accessing the chest cavity, opening the embolized pulmonary artery and/or its branches and removing the clot is also possible.

The prior approaches to treatment, however, are lacking. For example, the use of agents such as anticoagulants and/or thrombolytics to reduce or remove a pulmonary embolism typically takes a prolonged period of time, e.g., hours and even days, before the treatment is effective. In some instances, such agents can cause hemorrhage in a patient. Moreover, the known mechanical devices for removing an embolism are typically highly complex, prone to cause undue trauma to the vessel, and can be difficult and expensive to manufacture.

Lastly, the known treatment methods do not emphasize sufficiently the goal of urgently restoring blood flow through the thrombus once the thrombus has been identified. In other words, the known methods focus primarily and firstly on overall clot reduction and removal instead of first focusing on relief of the acute blockage condition followed then by the goal of clot reduction and removal. Hence, known methods are not providing optimal patient care, particularly as such care relates to treatment of a pulmonary embolism.

SUMMARY

In view of the foregoing, several embodiments of the present technology to provide a method and system that initially restores an acceptable level of oxygenated blood to the patient's circulatory system followed by safe and effective removal of the thrombus.

Several embodiments of the present technology treat pulmonary embolism in a minimally invasive manner.

Several embodiments of the present technology can also provide a system that does not cause undue trauma to the vessel.

BRIEF DESCRIPTION OF THE DRAWINGS

These and other objects, aspects, features and advantages of which the present technology is capable will be apparent from the following description of embodiments of the present technology, reference being made to the accompanying drawings, in which

FIGS. 15-18 are side views of guide catheters for use with clot treatment devices and methods in accordance with embodiments of the present technology.

FIG. 19 is a side view of a clot treatment device including arcuate clot engagement members configured in accordance with an embodiment of the present technology.

FIGS. 20-23 show embodiments of arcuate clot engagement members configured in accordance with the present technology.

DETAILED DESCRIPTION

Figure 1A:
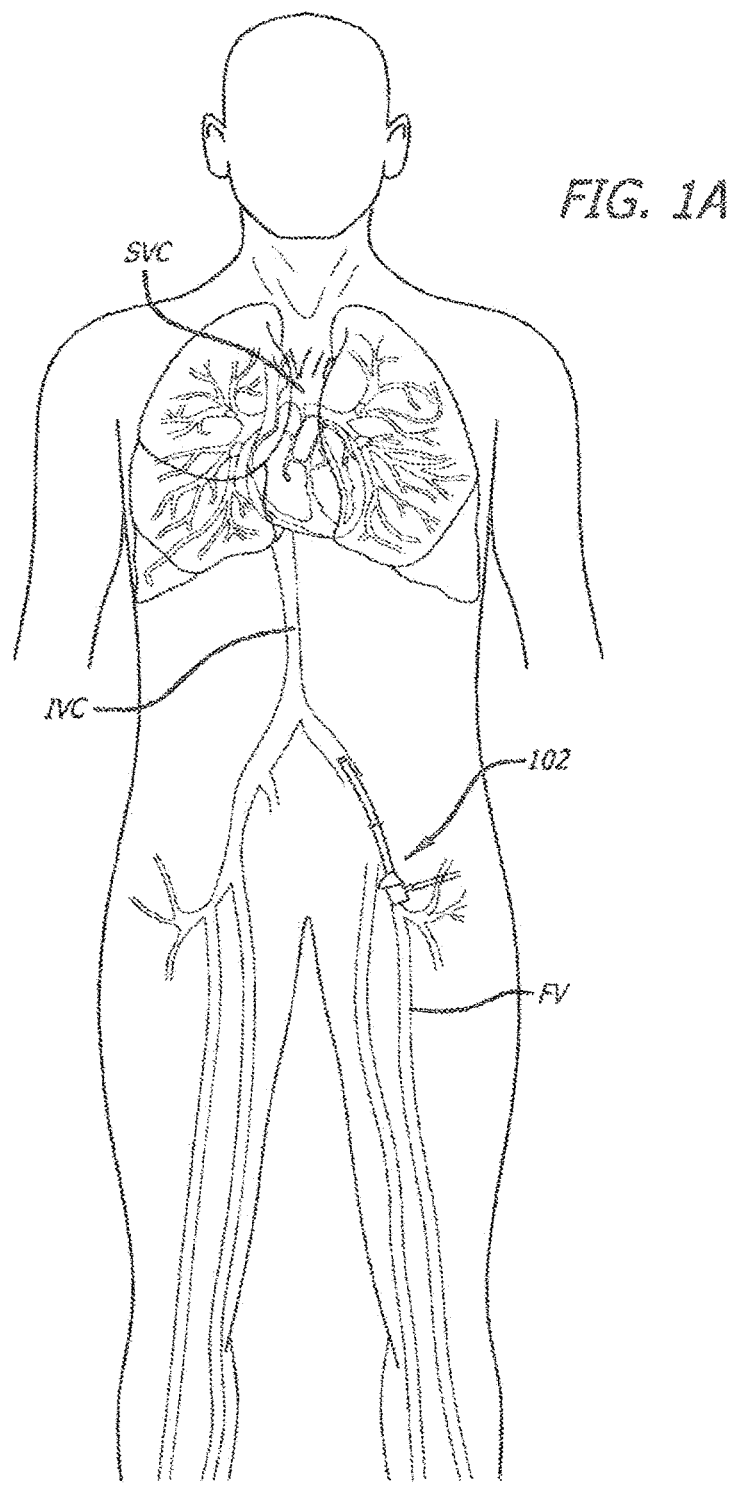
FIG. 1A is a schematic view of a patient with a pulmonary embolism.

Specific embodiments of the present technology will now be described with reference to the accompanying drawings. This present technology may, however, be embodied in many different forms and should not be construed as limited to the embodiments set forth herein; rather, these embodiments are provided so that this disclosure will be thorough and complete, and will fully convey the scope of the present technology to those skilled in the art. The terminology used in the detailed description of the embodiments illustrated in the accompanying drawings is not intended to be limiting of the present technology. In the drawings, like numbers refer to like elements.

Figure 1B:
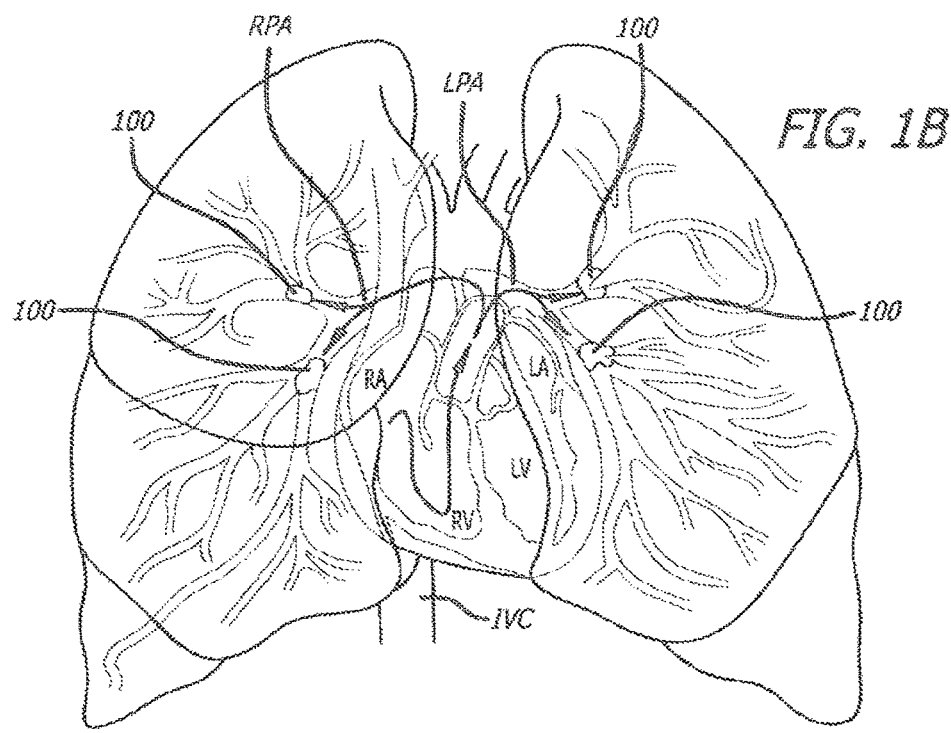
FIG. 1B is an enlarged view of the lung area of the patient depicted in FIG. 1A.
Figure 1C:
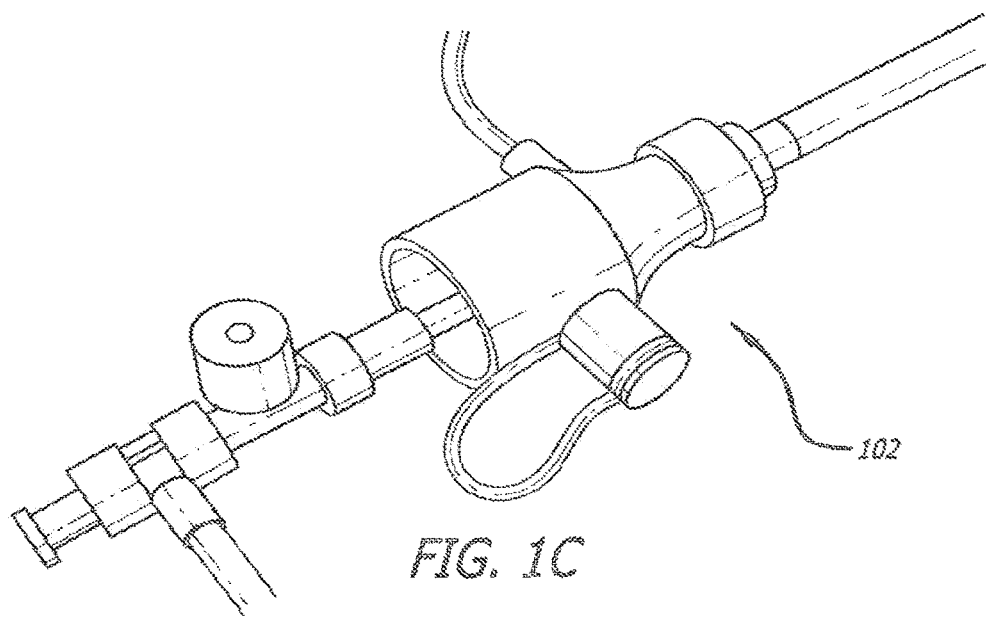
FIG. 1C is an enlarged view of the introducer device depicted being used in the femoral vein of the patient in FIG. 1A.

Referring to FIGS. 1A-1C, these drawings show the typical locations in a human patient where clots 100, such as pulmonary embolisms, thromboses, or other obstructions, occur in the pulmonary arteries and further discloses the pathway through which access to such clots 100 is achieved. In particular, an introducer device (e.g., a hemostatic valve) 102 which supports relatively large diameter devices is inserted into the patient into the femoral vein FV in the pelvic area of the patient. The tools and devices needed to treat the pulmonary embolism are then inserted through the introducer 102 into the femoral vein FV through the inferior vena cava IVC to the patient's heart.

It will be understood, however, that other access locations into the venous circulatory system of a patient are possible and which are consistent with the present technology. For example, the user can gain access through the jugular vein, the subclavian vein, the brachial vein or any other vein that connects or eventually leads to the superior vena cava. Use of other vessels that are closer to right atrium RA of the patient's heart may be attractive as this will reduce the length of the instruments needed to reach the pulmonary embolism.

Figure 2:
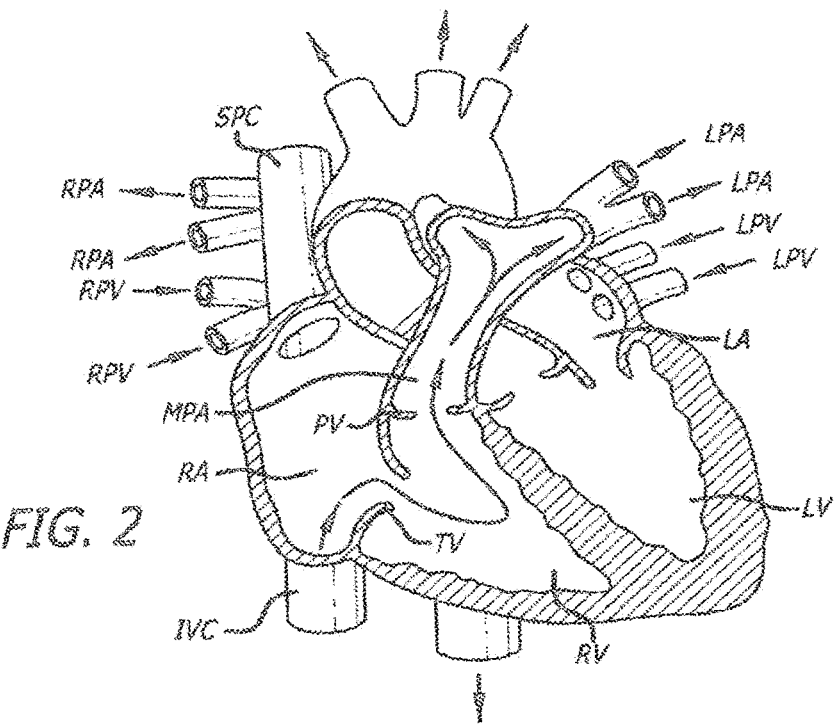
FIG. 2 is a cross-sectional view of a patient's heart.
Figure 3:
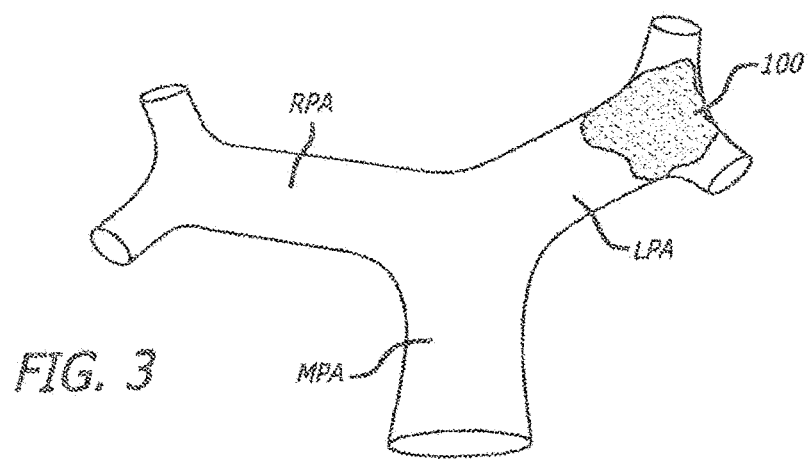
FIG. 3 is a perspective view of a patient's main pulmonary artery and right and left pulmonary arteries with a clot located in the left pulmonary artery.

Referring to FIGS. 2 and 3, the tools/devices are then guided through the right atrium RA through the tricuspid valve TV, into the right ventricle RV, through the pulmonary valve PV into the main pulmonary artery (MPA). Depending on the location of the embolism 100, the tools/devices are then guided to one or more of the branches of the right pulmonary artery RPA or the left pulmonary artery LPA, including deeper branches thereof, to the location of the pulmonary embolism 100.

Figure 4:
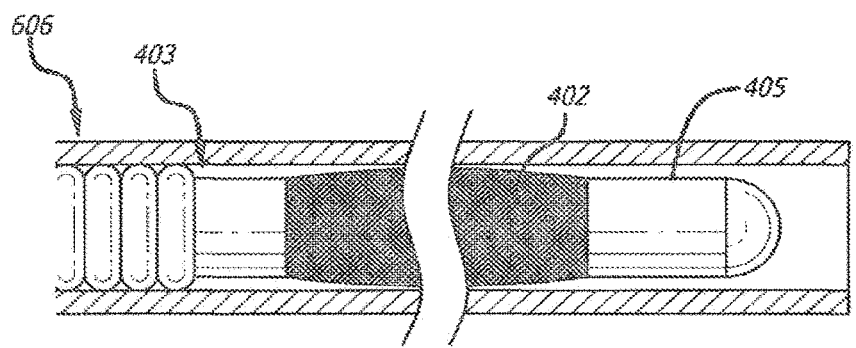
FIG. 4 is a cross-sectional view of an embodiment of a clot treatment device in accordance with the present technology in a compressed, undeployed state.

Referring to FIG. 4, an embodiment of a clot treatment device 402 for restoring blood flow through the clot 100 and for removing at least a portion of the clot is depicted in its undeployed, or compressed state. The device 402 is constrained by a delivery catheter 606. In many embodiments, the device 402 comprises a braided material having ends that are captured distally by a tip 405 and proximally by an attachment member 403 that connects to a wire 401 configured to push and/or pull the clot treatment device 402.

In alternative embodiments, the clot treatment device 402 may be an "over the wire" device, in which case, the wire 401 is a tube or coil having a lumen, and the attachment member 403 and the tip 405 have a hollow central lumen for receiving a guide wire.

In yet a further embodiment, the distal end of the clot treatment device shall have a flexible, atraumatic extension from the device. In an alternative embodiment, the tip 405 is tapered to better penetrate the clot material in the vessel.

In preferred embodiments the clot treatment device 402 of the present technology has a generally cylindrical shape that, during use, creates a flow lumen through the clot material that restores significant blood flow across a clot. The treatment device 402 is not, however, limited to a generally cylindrical shape. For example, the shape can be generally conical, generally concave or generally convex along its axis such that the clot treatment device 402 creates a lumen for restoring the blood flow.

Figure 5A:
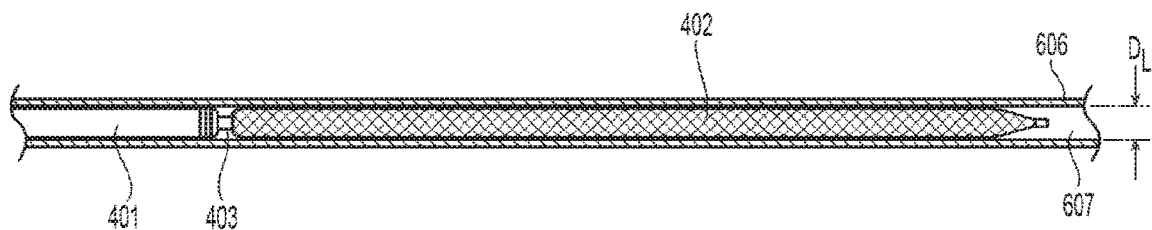
FIG. 5A is a side cross-sectional view of a clot treatment device in a compressed, undeployed state within a delivery catheter in accordance with the present technology.
Figure 5B:
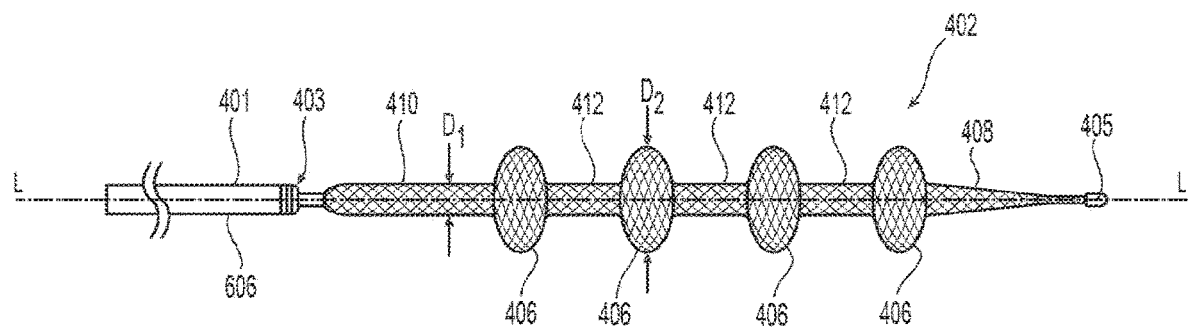
FIG. 5B is a top view of a clot treatment device in a deployed state in accordance with the present technology.

FIG. 5A shows one embodiment of the treatment device 402 in a low-profile, undeployed state in which the clot treatment device is configured to fit within a delivery catheter, and FIG. 5B shows the clot treatment device 402 of FIG. 5A in a deployed state configured to restore blood flow and capture clot material for removal. Referring to FIG. 5A, the clot treatment device 402 is compressed to fit within the diameter OL of a lumen 607 of the delivery catheter 606 in the undeployed state. In the deployed state shown in FIG.

58, the clot treatment device 402 has a plurality of capture elements, such as a series of radially extending capture portions 406 which are separated from each other by flow restoration portions 412. The flow restoration portions 412 are configured to expand outwardly from the low-profile undeployed state within the delivery catheter lumen 607 to a first cross-sectional dimension 01 (e.g., diameter) in the deployed state. For example, the flow restoration portions 412 can be generally cylindrical braided sections that expand radially outward from the undeployed stated to the deployed state. In many applications, the first cross-sectional dimension 01 is greater than the diameter OL of the delivery catheter lumen 607. The capture portions 406 are configured to expand outwardly from the low-profile undeployed state to a second cross-sectional dimension 02 greater than the first cross-sectional dimension 01 in the deployed state. As explained in more detail below, the capture portions 406 can project into the clot such that they extend transverse to a longitudinal axis L-L of the clot treatment device 402, while the flow restoration portions 412 expand radially outward into the clot to open a passage through which blood can quickly resume flow through the vessel. The clot treatment device 402 can be porous so blood flows therethrough. In this regard, many embodiments of the clot treatment device 402 are made from a mesh or braided material. The material can be a super-elastic material such as Nitinol or an alternative material such as cobalt chrome alloy. The device can be made from a wire lattice, wire braid or stent. Specific preferred embodiments are discussed throughout this specification.

Referring again to FIG. 58, the clot treatment device 402 can comprise a single mesh structure that is generally cylindrical in the low-profile undeployed state (shown in FIG. 5A). The series of radially extending capture portions 406 accordingly extend from the same mesh as the corresponding series of flow restoration portions 412. The flow restoration portions 412 can be generally cylindrical sections in the deployed state, or in other embodiments the flow restoration portions 412 may taper in the distal direction individually and/or collectively to form a conical lumen (not shown). Each of the capture portions 406 can be a radial or otherwise transversely projecting disk that projects outward relative to the flow restoration portions 412.

The clot treatment device 402 can self-expand from the undeployed state to the deployed state. For example, the clot treatment device 402 can be a shape-memory material, such as Nitinol, and may be formed as a braid or a stent that is set to have the expanded configuration of the deployed state shown in FIG. 58 unless it is otherwise deformed or constrained, such as being elongated along the longitudinal axis L-L to fit within the delivery catheter 606 as shown in FIG. 5A. In other embodiments, the clot treatment device 402 can be actuated by a push/pull wire, tube or coil to move from the low-profile undeployed state to the expanded deployed state as explained in more detail below with reference to FIGS. 10-12.

FIGS. 1-6F show embodiments of methods for restoring blood flow and retrieving/removing clot material with the clot treatment device 402 in a body lumen L.

Figure 6A:
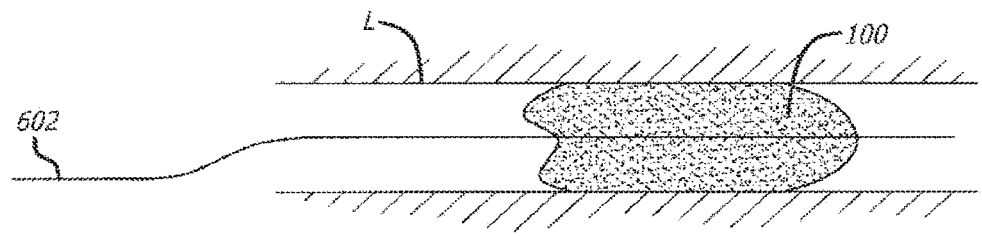
FIGS. 6A-6F are a series of cross-sectional views of embodiments of the method and device of the present technology.
Figure 6B:
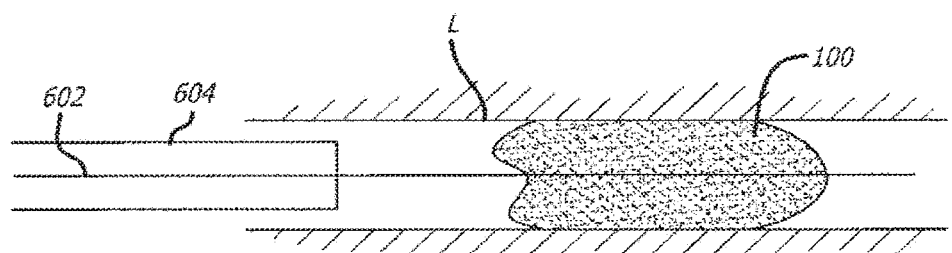
Figure 6C:
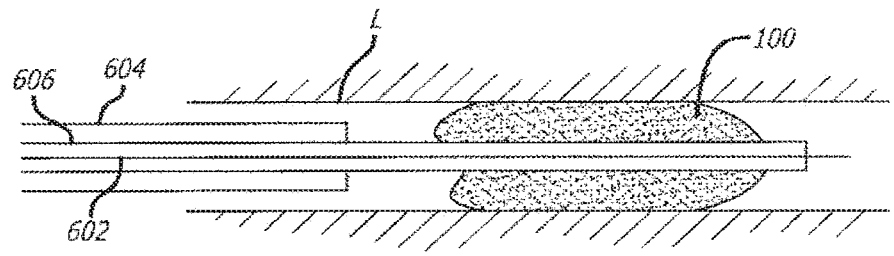
Figure 6D:
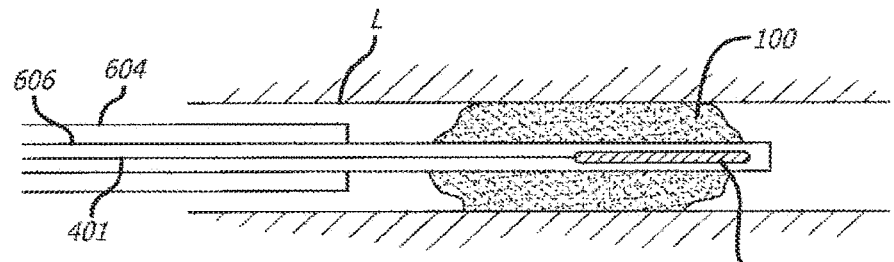

Referring to FIGS. 1A, 1B and 6A, a guide wire 602 is inserted into the patient via an introducer 102 and maneuvered through the femoral vein FV into the inferior vena cava IVC to the heart. As stated above, access can also be achieved through one of the veins leading to the superior vena cava SVC. The guide wire 602 is then urged through the right atrium RA, through the tricuspid valve TV, through the right ventricle RV, through the pulmonary valve PV to the main pulmonary artery MPA and then to a location of the clot 100 in one of the branches or lumens L of either the right or left pulmonary artery RPA, LPA. In several embodiments, the guide wire 602 is extended through the clot 100 in the body lumen L as shown in FIG. 6A.

Referring to FIG. 68, a guide catheter 604 is placed over the guide wire 602 and moved to a location where a distal end of the guide catheter 604 is positioned proximal to the clot 100. At this point, the guide wire can optionally be withdrawn. However, in the embodiment shown in FIG. 6C, the guide wire 602 remains positioned through the clot 100 and a delivery catheter 606 is then moved through the. guide catheter 604 over the guide wire 602 and pushed through the clot 100.

Figure 6E:
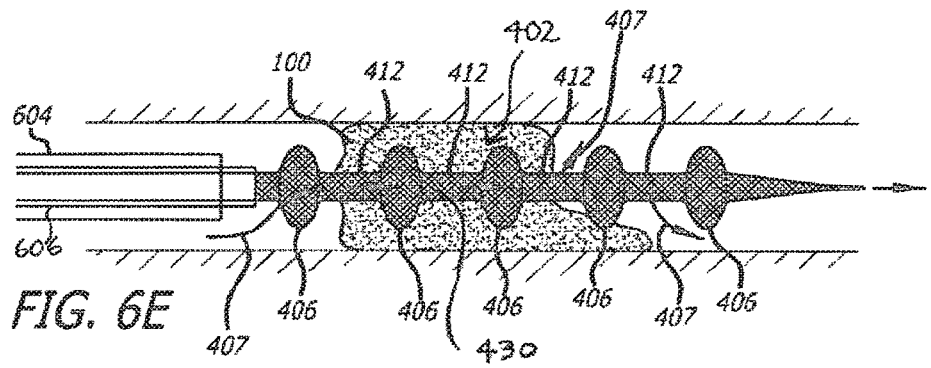
Figure 10:
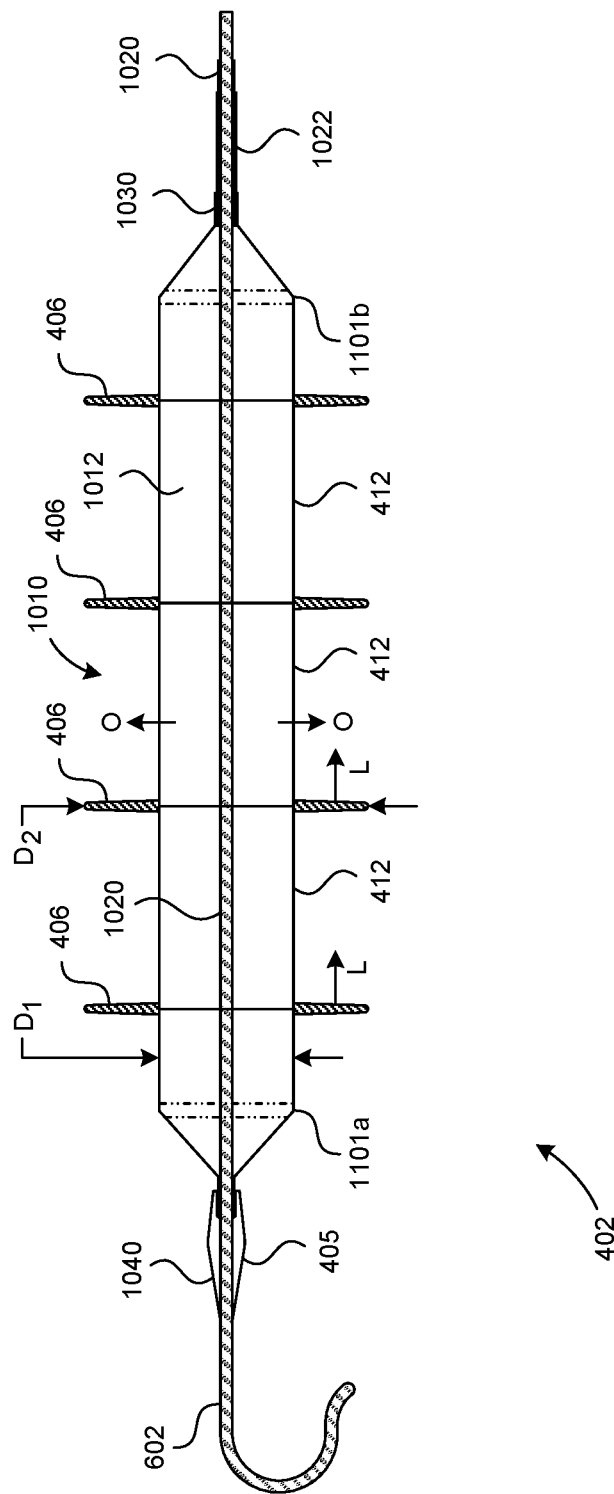
FIG. 10 is a cross-sectional view of a clot treatment device in accordance with another embodiment of the present technology.

Referring to FIG. 60, the guide wire 602 is then withdrawn and the clot treatment device 402 in its undeployed (i.e., compressed) state is then moved through the delivery catheter 606 until it is positioned at the distal end of the delivery catheter 606. Alternatively, if an over-the-wire device configuration (as shown in FIG. 10) is used, the guide wire 602 may be left in place while the treatment device 402 is deployed and retracted. Referring to FIG. 6E, the delivery catheter 606 is then retracted in a proximal direction while maintaining forward pressure on the clot retrieval device 402 via the pusher wire 401 so that the clot treatment device 402 is exposed and released from the delivery catheter 606. The clot treatment device 402 radially expands into the clot 100 and, in some embodiments, at least a portion of the clot treatment device 402 expands distal of the clot 100. For example, at least one of the radially extending capture portions 406 of the clot treatment device 402 is located distal to the clot 100 upon expansion of the clot treatment device 402. Additionally, the flow restoration portions 412 between the capture portions 406 also expand outwardly against a portion of the clot 100 to form a flow passage 430 though the clot treatment device 402.

The clot treatment device 402 accordingly restores blood flow through the clot 100 immediately or at least quickly after expanding to the deployed state as shown by arrows 407 in FIG. 6E. More specifically, the blood freely moves through the mesh of the clot treatment device 402, travels through the device lumen and exits the clot treatment device 402 distal to the clot 100. As a result, the acute condition of blockage is mediated thus immediately improving the circulation of oxygenated blood in the patient.

The restoration of blood flow is anticipated to equate with restoration of a substantial portion of the normal blood flow rate for the patient. In less severe. e.g., "sub-massive," pulmonary embolism patients, the clot treatment device 402 may increase blood flow rate by at least about 50 mllmin, at least about 150 mllmin or between about 100 to 250 mllmin. In severe, e.g., "massive," pulmonary embolism patients, a larger amount of the pulmonary artery flow is compromised. Hence, in some embodiments, at least about 500 ml/min of blood flow rate may be restored. Moreover, at least a portion of the flow restoration is expected to occur prior to the removal of the clot 100, or any portion thereof.

The restoration of blood flow by the clot treatment device 402 can be achieved in a low pressure environment. For example, the pressure in the target vessel can be less than 60 mmHg and the blood can be venous blood, substantially non-oxygenated blood or low oxygenated blood.

In addition to restoring blood flow, the expansion of the clot treatment device 402 also deforms the clot material by pushing, penetrating and/or otherwise cutting into the clot material. This enhances the subsequent removal of the clot 100 since portions of the clot 100 may be captured and retained (1) between the radially extending portions 406; (2) through the pores of the mesh forming the radially extending portions 406; (3) along the longitudinal cylindrical sections 412 between the radially extending portions 406 of the removal device 402; and (4) within the clot treatment device 402 itself.

As can be understood from the above description and figures, the deployment of the clot treatment device 402 results in an outwardly expanding generally cylindrical force being urged against an inner surface of the clot 100 because the flow restoration portions 412 expand to the first cross-sectional dimension D1 greater than the diameter DL of the delivery catheter lumen 607. This force pushes the clot material outwardly and creates a lumen through which blood flow is restored. As can also be appreciated, the presence of the radially extending capture portions 406 on the clot treatment device 402 causes the outwardly expanding generally cylindrical force to vary in magnitude along the axis of the clot treatment device 402. The force on the clot material may be greater at the locations of the radially extending capture portions 406.

In braided embodiments of the clot treatment device 402, deployment/expansion of the device leads the filaments of the braid to change their angular orientation with respect to the axis of the device. This angular change may improve or enhance adherence of clot material to the clot treatment device 402.

Figure 6F:
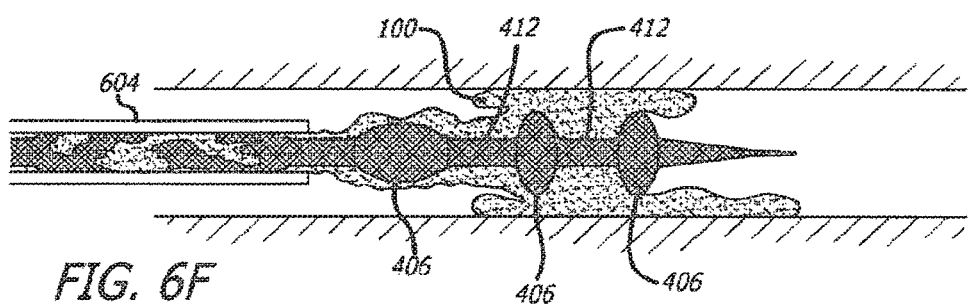

After the clot treatment device 402 has been expanded and blood flow restored, the user then retracts the clot treatment device 402 in a proximal direction as shown in FIG. 6F. Since the capture portions 406 extend transverse to the longitudinal dimension of the vessel, the capture portions 406 form transverse surfaces relative to the force exerted against the clot 100 as the clot treatment device 402 is pulled in the proximal direction. The capture portions 406 accordingly enhance the ability of the clot treatment device 402 to securely dislodge and retain the clot 100 as the clot treatment device 402 is moved axially along the vessel to retrieve the clot 100 from the patient. In one embodiment, the clot treatment device 402 and the delivery catheter 606 are pulled back simultaneously into the guide catheter 604. This is followed by the entire apparatus (e.g., clot treatment device 402, delivery catheter 606 and guide catheter 604) being withdrawn through the heart and the venous circulation and out from the body.

As further shown in FIG. 6F, the clot treatment device 402 may elongate as it is being withdrawn into the guide catheter 604 due to the resistance it encounters from the presence of clot material of the clot 100. The presence of the radially extending portions 406 may allow elongation that enhances the capability of the device 402 to capture the maximum amount of clot material. This is further discussed below with respect to the surface area and expansion ratio of preferred embodiments of the clot treatment device 402.

It will be appreciated that variations in the above-described method are contemplated. For example, in certain circumstances a guide catheter 604 may not be necessary or desirable and the user may choose to use only the delivery catheter 606 for placing and manipulation of the clot treatment device 402. As a further example, the clot may be of such a nature that the user may desire repeat the above-described process, or at least portions of it, in order to more fully remove the clot 100 or clot material.

Figure 7A:
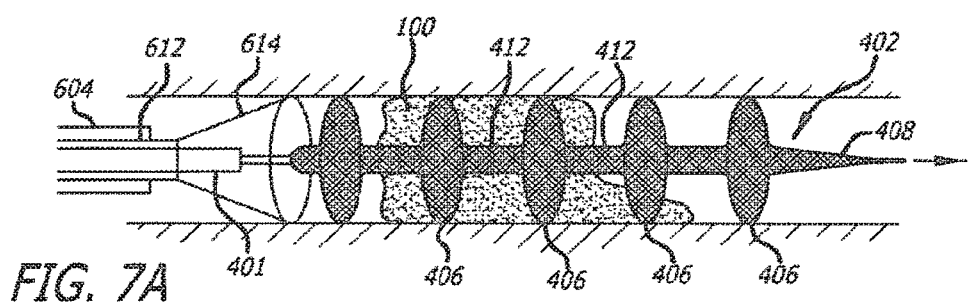
FIGS. 7A-7B are a series of cross-sectional views of embodiments of the method and device of the present technology.
Figure 7B:
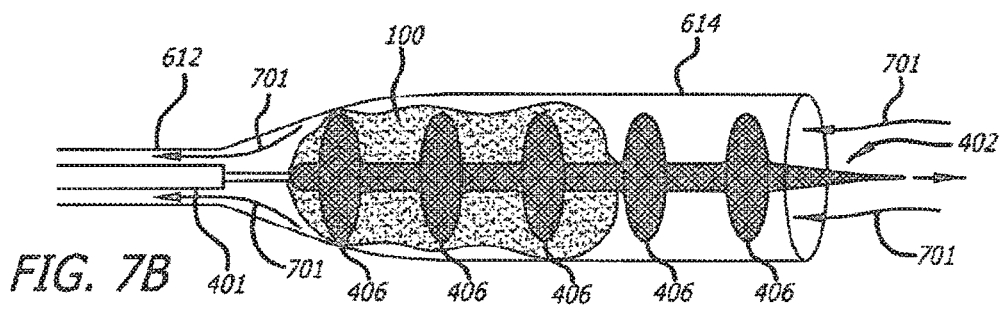

Referring next to FIGS. 7A-78, it may be advantageous to include the use of a collection or funnel catheter 612 to assist in the removal of the clot 100. Such a funnel catheter 612 has an expandable portion 614 at its distal end and may be situated between the guide catheter 604 and the delivery catheter 608 or may be part of the guide catheter 604. In the presence of the collection catheter 612, the clot treatment device 402 is pulled proximally into the collection catheter 612 such that the clot or portions of it are captured within the collection catheter 612. In an alternative embodiment, the collection catheter 612 can be pushed distally over the clot treatment device 402 such that the collection catheter 612 captures the clot or portions thereof. If the collection catheter 612 is separate from the guide catheter 606, the collection catheter with the clot treatment device 402 is then pulled into the guide catheter for ultimate removal of all devices (and the clot) from the patient.

In certain circumstances, it may be advisable to remove the clot 100 without capturing it in the guide catheter 606 or the collection catheter 612 (if used) and remove the clot 100 by withdrawing the entire system, e.g., guide catheter 605, delivery catheter 604, clot treatment device 402 and collection catheter 612 (if used) simultaneously.

In several embodiments, the expandable portion 614 of the collection catheter 612 is a conical funnel or other tapered member constructed from a mesh, braid or stent structure. Such structure assists in retrieving and containing the clot material in the withdrawal process. In yet further preferred embodiments, the collection catheter 612 contains structural features to assist in the expansion of the expandable portion 614 and to hold the expandable portion 614 open towards the wall of the blood vessel. Such features (not shown) include interwoven support struts, self expanding material (e.g., Nitinol), longitudinal wire supports, stent supports, polymeric webbing, etc.

Figure 8:
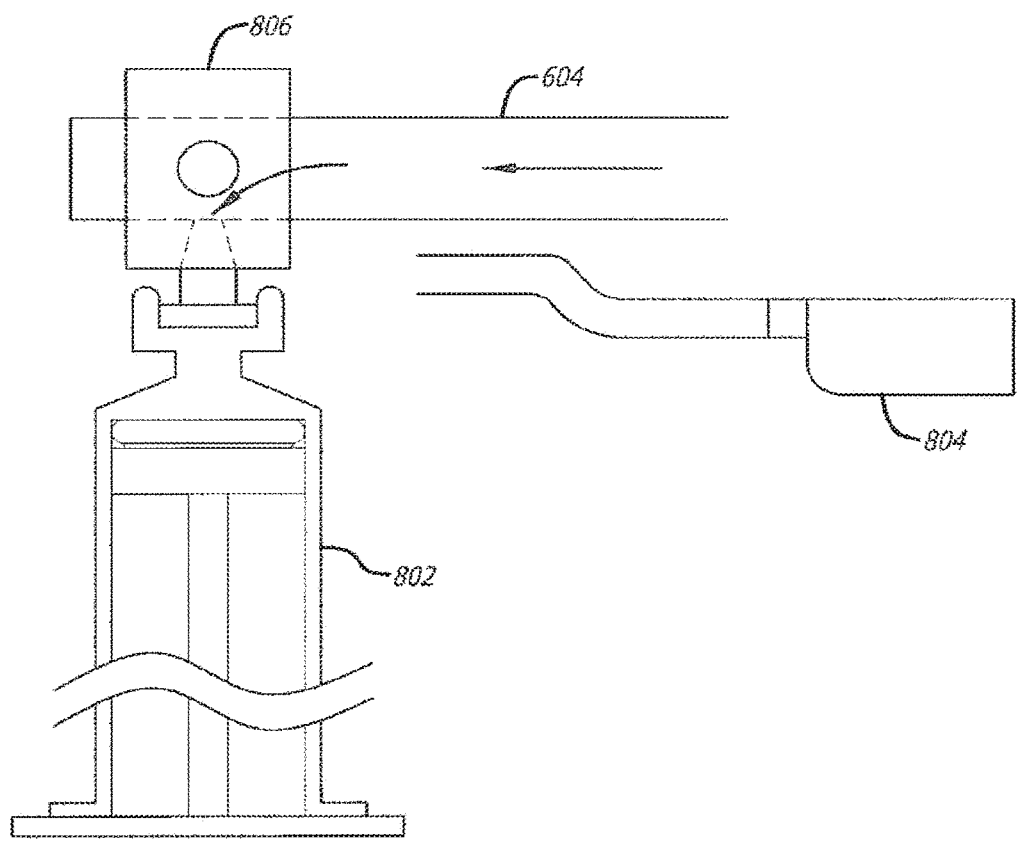
FIG. 8 is a cross-sectional view of another embodiment of the method and device of the present technology; and, FIGS. 9A-9H show cross-sectional views of embodiments of a clot treatment device in accordance with the present technology.

In another embodiment of the present invention, a vacuum apparatus may be used to aid in the removal of the clot material. Referring to FIG. 8, a syringe 802 is shown connected to a vacuum manifold 806 that is in fluid communication with the proximal end of the guide catheter 604. At the time the clot treatment device 402 (and clot material) is being withdrawn into the guide catheter 604 (or the collection catheter 612), vacuum is applied by pulling on the syringe. Alternative sources of vacuum 804 are also acceptable, e.g., a vacuum pump. A system is also contemplated whereby vacuum is actuated automatically when the clot treatment device 402 (and the clot material) is being withdrawn. A representation of the effect of the use of vacuum can be seen with reference to FIG. 78 which shows how vacuum causes flow 701 into the catheter 612.

Referring now to FIGS. 9A-9H, alternative preferred embodiments of the clot treatment device 402 are disclosed.

Figure 9A:
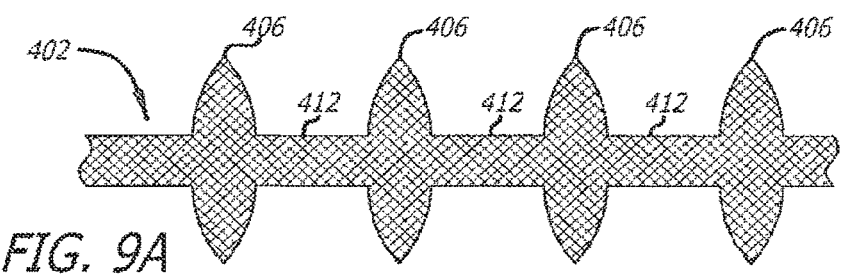
Figure 9B:
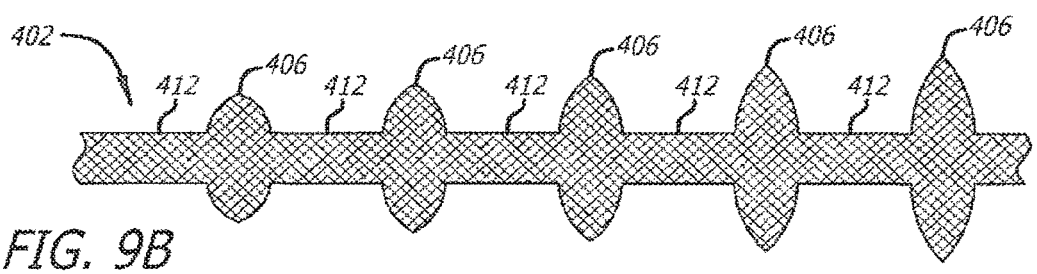

Referring to FIG. 9A, the radially extending portions 406 between the generally cylindrical sections 412 of the clot treatment device 402 are defined by a cylindrical disk shape with a rounded triangular cross-section.

Referring to FIG. 98, the radially extending portions 406 between the generally cylindrical sections 412 of the clot treatment device 402 are defined by a cylindrical disk shape with a rounded triangular cross-section wherein the diameter of the disk increases along the length of the device 402 thus forming a conical exterior extent.

Figure 9C:
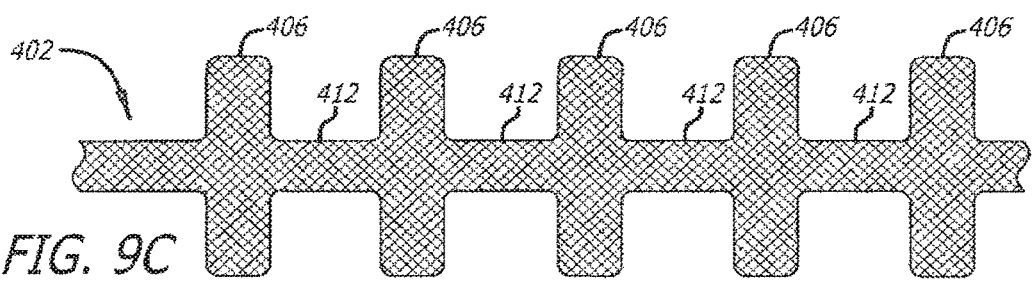
Figure 9D:
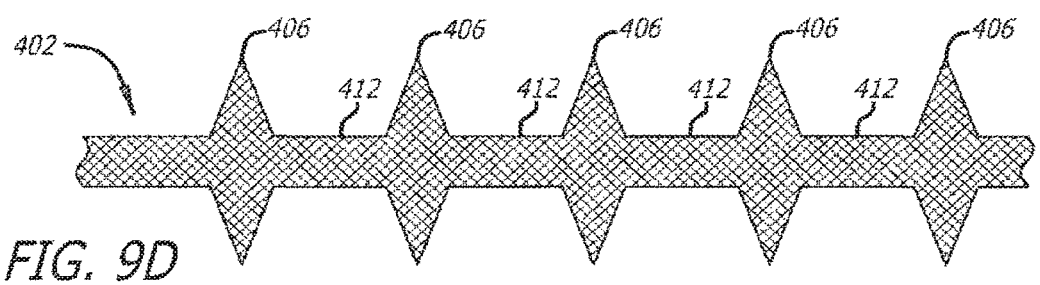

Referring to FIG. 9C, the radially extending portions 406 between the generally cylindrical sections 412 of the clot treatment device 402 are defined by a cylindrical disk shape with a rectangular cross-section.

Referring to FIG. 90, the radially extending portions 406 between the generally cylindrical sections 412 of the clot treatment device 402 are defined by a cylindrical disk shape with a linear (non-rounded) triangular cross-section.

Figure 9E:
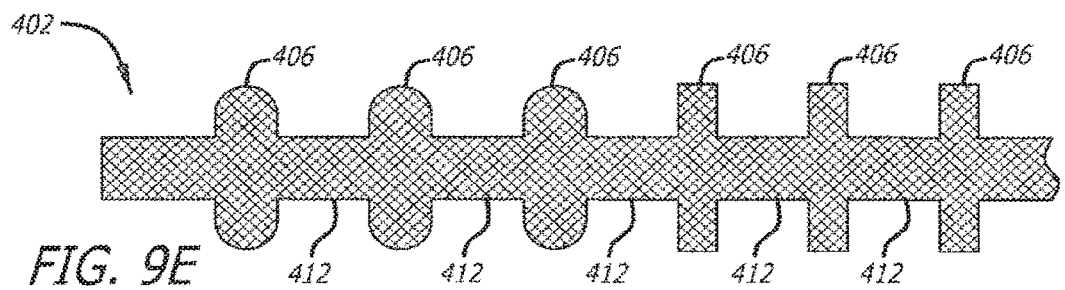

Referring to FIG. 9E, some of the radially extending portions 406 between the generally cylindrical sections 412 of the clot treatment device 402 are defined by a cylindrical disk shape with a rounded cross-section and others have a rectangular cross section.

Figure 9F:
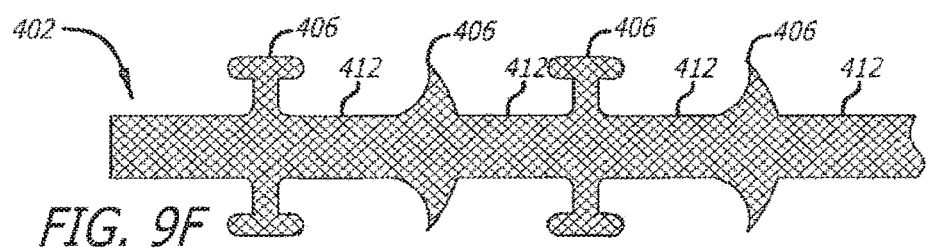

Referring to FIG. 9F, the radially extending portions 406 between the generally cylindrical sections 412 of the clot treatment device 402 alternate between cylindrical disk shape with a T-shaped cross-section and a flare-shaped cross-section.

Figure 9G:
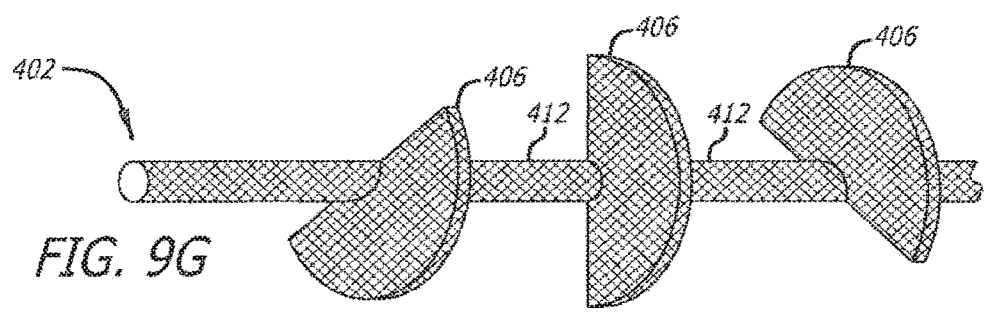

Referring to FIG. 9G, the radially extending portions 406 between the generally cylindrical sections 412 of the clot treatment device 402 are defined by a partial cylindrical disk shapes.

Figure 9H:
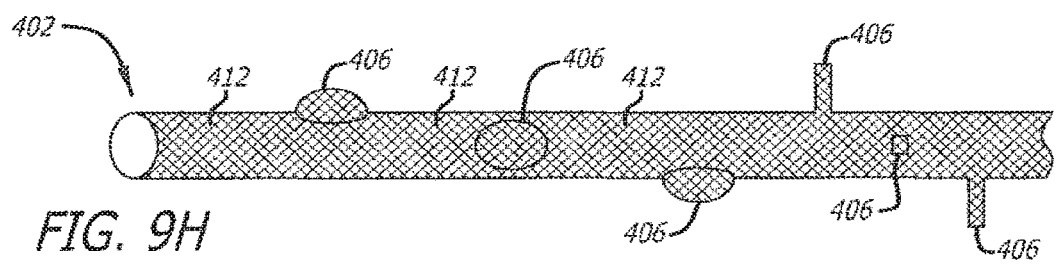

Referring to FIG. 9H, the radially extending portions 406 between the generally cylindrical sections 412 of the clot treatment device 402 are defined by tabs and bumps or protuberances arising from the cylindrical surface of the device 402.

FIG. 10 is a cross-sectional view of another embodiment of the clot treatment device 402 in accordance with the technology having an expandable member 1010, an elongated inner member 1020, and an elongated outer member 1022. The expandable member 1010 is configured to have an undeployed state in which the expandable member 1010 is elongated axially to have a low profile that fits within a delivery catheter as shown in FIG. 4. The expandable member 1010 is further configurable into a deployed state in which the expandable member 1010 forms a flow channel 1012 for restoring blood flow through the region obstructed by the clot. The expandable member 1010, for example, can be a mesh, braid, stent-type device, or other suitable member through which blood flows in the deployed state. In one embodiment, the expandable member 1010 is a continuous braid formed from a shape-memory material that has been heat set such that, in the deployed state, the expandable member 1010 has a plurality of flow restoration portions 412 that expand to the first cross-sectional dimension 01 to form the flow channel 1012 and a plurality of capture portions 406 that expand to the second cross-section dimension 02 greater than the first cross-sectional dimension 01. The flow restoration members 412 accordingly exert an outward force (arrows 0) against clot material (not shown) to create the flow channel 1012, and the capture portions 406 accordingly exert a longitudinal force L (arrows L) against the clot material as the clot treatment device 402 is moved proximally.

The elongated inner member 1020 can be a tube or coil having inner lumen configured to receive the guidewire 602 for over-the-wire or rapid exchange delivery of the expandable member 1010 to the clot. The outer elongated member 1022 can be a tube or coil having a lumen configured to receive the inner elongated member 1020 such that the inner elongated member 1020 and/or the outer elongated member 1022 can move relative to each other along the longitudinal dimension of the clot treatment device 402.

Figure 11:
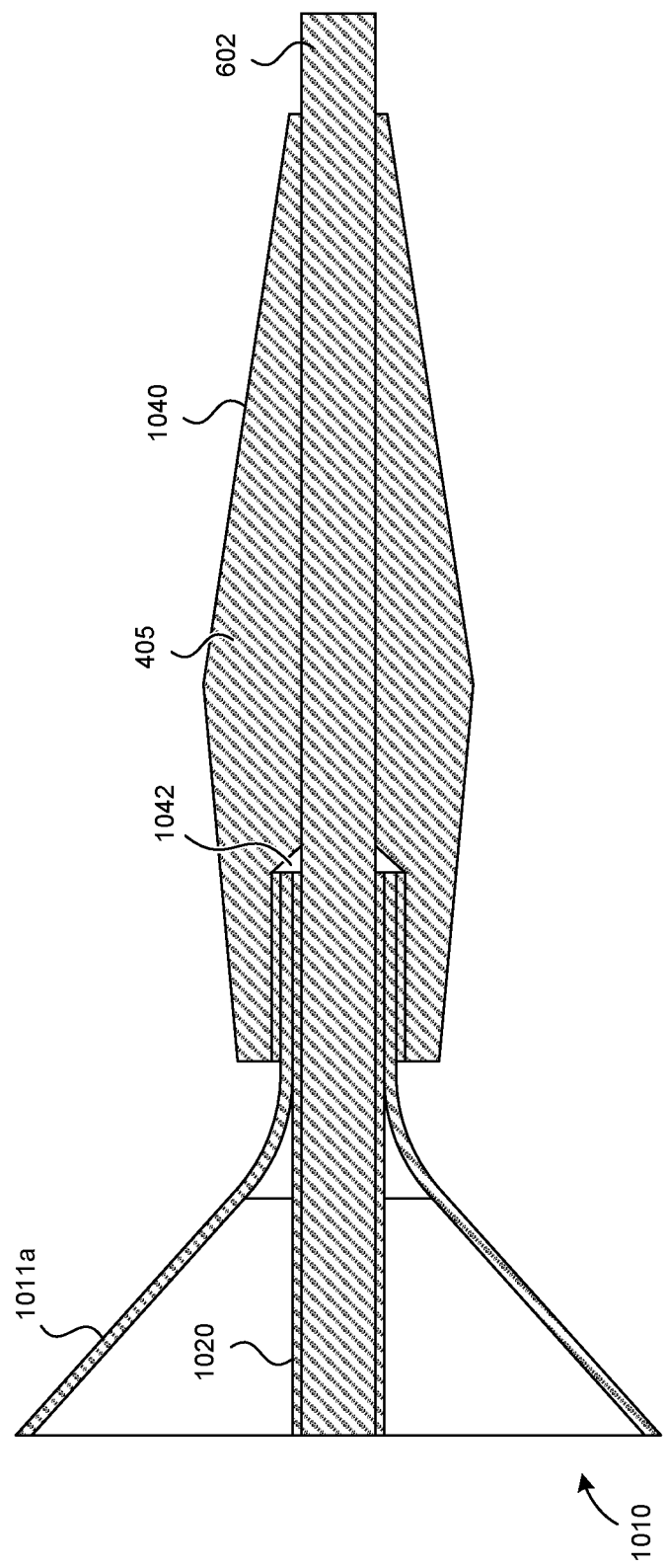
FIGS. 11 and 12 are detailed cross-sectional views of a distal portion and a proximal portion, respectively, of an expandable member of a clot treatment device in accordance with an embodiment of the present technology.
Figure 12:
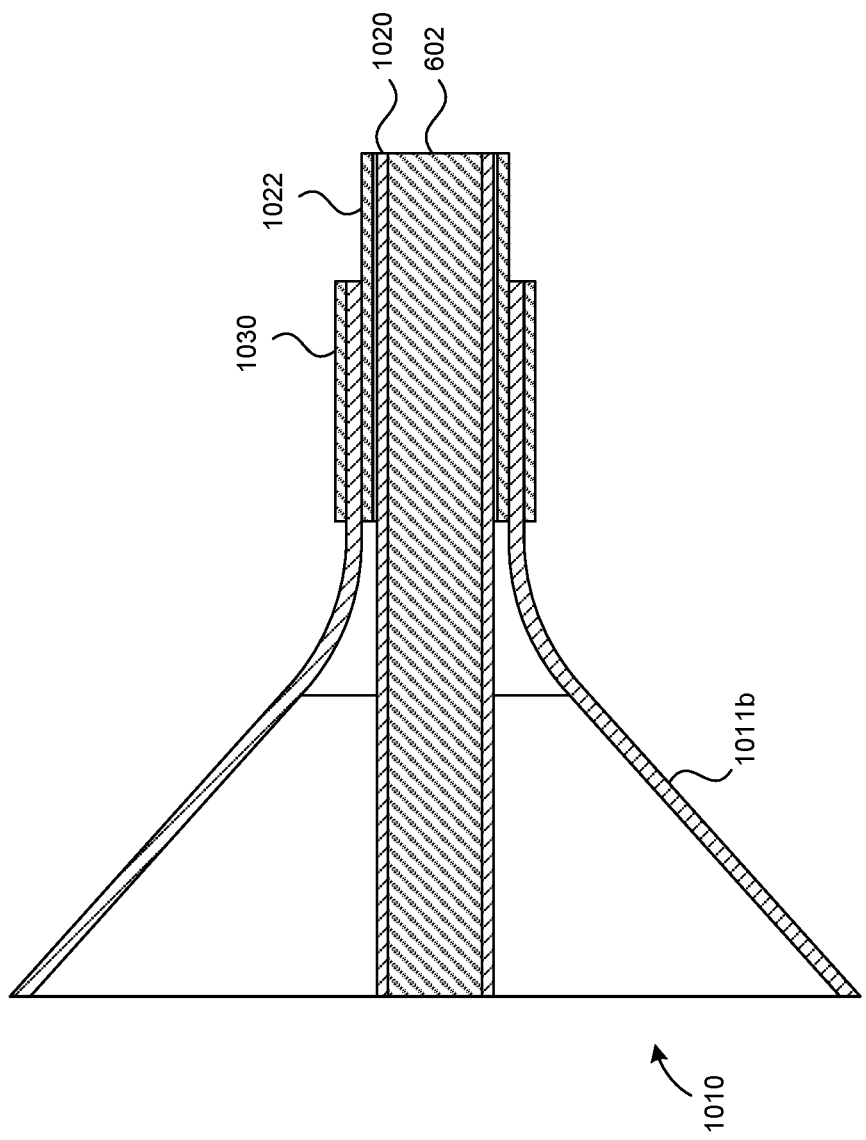

FIGS. 11 and 12 are detailed views of a distal portion 1011a (FIG. 11) and a proximal portion 1011b (FIG. 12) of the expandable member 1010 of the clot treatment device 402 shown in FIG. 10. Referring to FIG. 11, the distal portion 1011a is attached to a distal end of the inner elongated member 1020 by the tip 405. The tip 405 can be blunt as described above with reference to the embodiment of the clot treatment device 402 shown in FIG. 4, or the tip 405 can have a tapered distal portion 1040 configured to pass through the clot as shown in FIG. 11. Additionally, the tip 405 can have a proximal opening 1042 configured to receive the distal end of the inner elongated member 1020 and the distal end of the expandable member 1010. Referring to FIG. 12, the proximal portion 1011b is attached to the distal end of the outer elongated member 1022 by a proximal hub 1030. For example, the distal and proximal portions 1011a and 1011b can be attached to the inner elongated member 1020 and the outer elongated member 1022, respectively, using welds, adhesives, crimping or clamping forces, and/or other suitable attachment mechanisms.

In the operation of the clot treatment device 402 shown in FIGS. 10-12, the expandable member 1010 can self-expand from the undeployed state to the deployed state without an actuator. For example, as a delivery catheter is drawn proximally to release the expandable member 1010, the inner elongated member 1020 can be held in place to hold the distal portion 1011a of the expandable member 1010 distally of the clot. As the distal end of the delivery catheter moves proximally, the outer elongated member 1022 will slide distally as the expandable member 1010 expands until the expandable member 1010 reaches its predetermined deployed size or otherwise reaches equilibrium with the clot. In other embodiments, the inner elongated member 1020 and/or the outer elongated member 1022 can be actuators that are moved proximally and/or distally to control the radial expansion and/or the radial contraction of the expandable member 1010.

Figure 13:
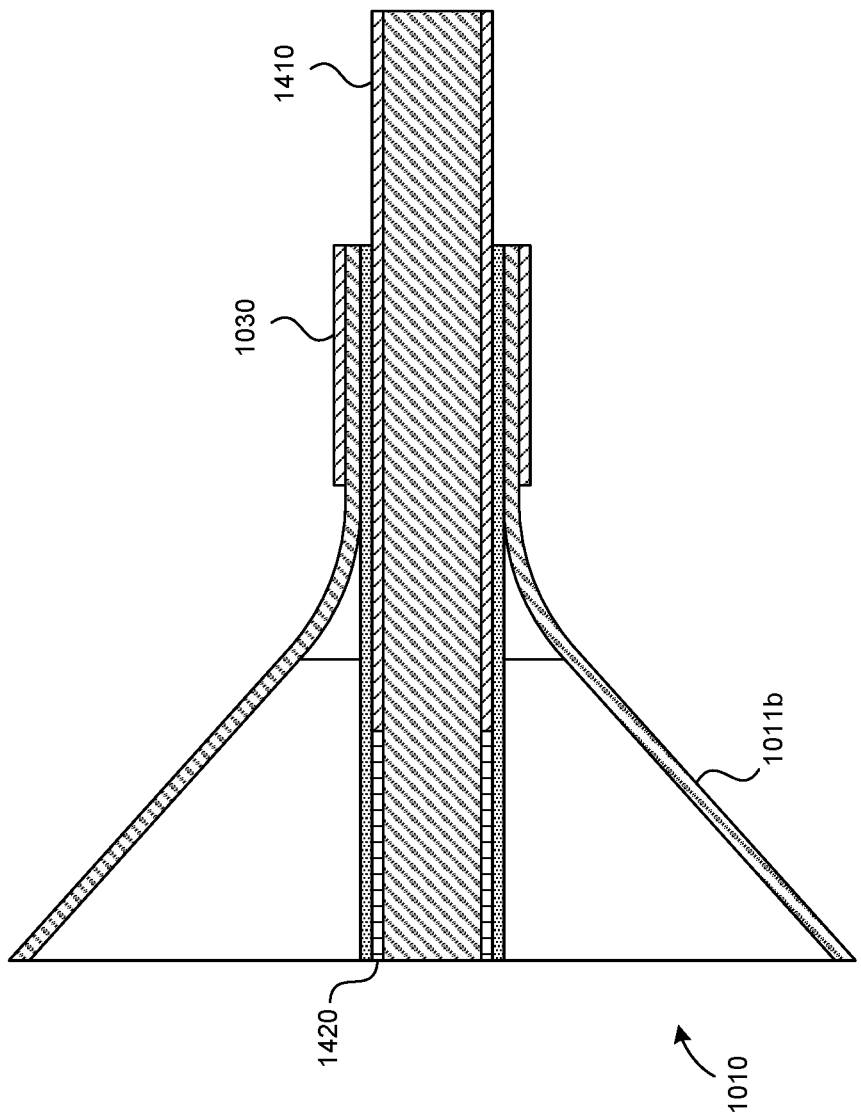
FIGS. 13 and 14 are detailed cross-sectional views of a proximal portion and a distal portion, respectively, of an expandable member of a clot treatment device in accordance with another embodiment of the technology.
Figure 14:
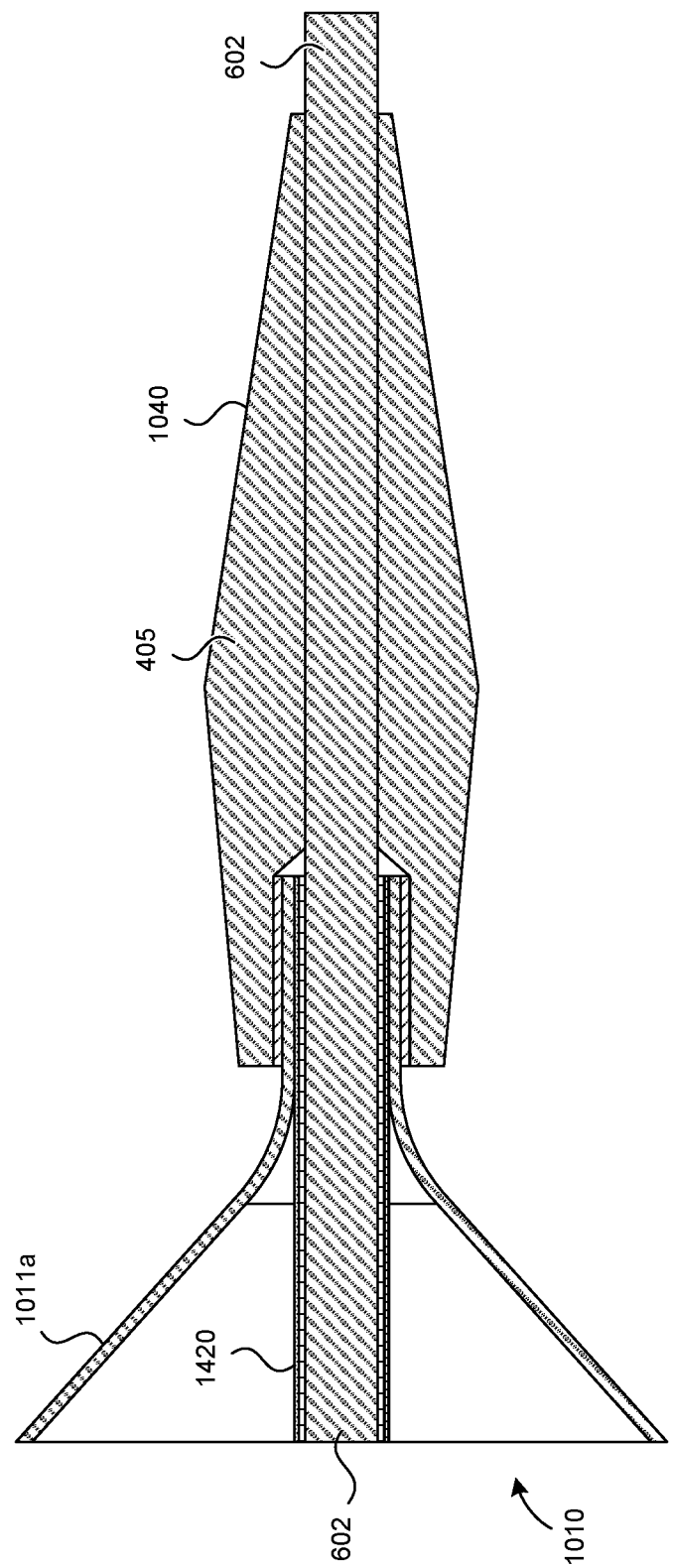

FIGS. 13 and 14 are detailed views of the proximal and distal portions 1011b and 1011a, respectively, of an expandable member 1010 and other components of a clot treatment device 402 in accordance with another embodiment of the technology. In this embodiment, the clot treatment device 402 has a proximal tube 1410 (FIG. 13) and an expansion element 1420 having one end attached to the proximal tube 1410 and another end attached to the distal portion 1011a (FIG. 14) of the expandable member 1010. The expansion element 1420, for example, can be a coil or spring that is stretched from its normal state when the expandable member 1010 is the low-profile, undeployed state inside the delivery catheter. As the distal portion 1011a and then the proximal portion 1011b of the expandable member 1010 are released from the delivery catheter, the expansion element 1420 contracts axially under its own stored spring force causing the expandable member 1010 to contract axially and expand radially outward. In the embodiments where the expandable member 1010 is self-expanding, the expansion element 1420 assists the expansion of the expandable member 1010. In other embodiments, the expandable member 1010 may not be self-expanding or may be inherently spring-biased into the low-profile undeployed state, and the expansion element 1420 can have enough stored energy when it is stretched in the low-profile undeployed state to pull the distal portion 1011a and the proximal portion 1011b of the expandable member 1010 toward each other and thereby radially expand the expandable member 1010.

In the foregoing embodiments, the radially extending capture portions 406 provide more surface area along the device than a device that is uniformly cylindrical. Moreover, the radially extending capture portions 406 extend transversely to the longitudinal dimension of the device to more effectively transfer the axial force as the device is moved axially along the vessel after deployment. Such increased surface area facilitates the treatment and/or retrieval of a much larger portion of the clot 100 than is generally feasible with a uniformly cylindrical device. For example, in a preferred embodiment of the clot treatment device 402, the device will have an external surface area between 1.5× and 6× the surface area of a uniformly cylindrical device of the same general diameter of the cylindrical sections 412. In other preferred embodiments the ratio will be 2× to 4×.

This is advantageous particularly during retraction of the clot treatment device 402 through the clot 100. As shown in FIG. 6F, the clot treatment device 402 may become elongated as it is being withdrawn through the clot 100. Such elongation causes the clot material to encounter greater surface area of the clot treatment device 402 than would otherwise occur with a device that was only generally cylindrical, i.e., that did not incorporate radially extending portions 406. Accordingly the clot treatment device 402 is particularly adept at capturing the maximum amount of clot material during withdrawal.

The clot treatment device 402 is intended for use in large vessels, i.e., vessels with a diameter greater than 8 mm. For example, the diameter of the pulmonary arteries typically range from 15 to 30 mm whereas the first branches of the pulmonary arteries typically range from 10 to 15 mm and the secondary and tertiary branches typically range from 5 to 10 mm. At the same time, however, it is important to minimize the size of catheter providing access to the clot 100. Accordingly, the clot treatment device 402 has a large expansion ratio. In a preferred embodiment the expansion ratio from the diameter of the cylindrical sections 412 in the collapsed state to the expanded state will be between 4 and 8. In another preferred embodiment the ratio will be between 5 and 7. The large expansion ratio also enables the formation of a flow channel in the clot 100 that is large, e.g., on the order of 4-8 mm.

The radially extending portions 406, in their fully expanded position are intended to have a size that matches the diameter of the target blood vessel. However, the diameters may be slightly larger than the vessel diameter so to apply greater radial force against the blood vessel (without causing trauma) in those circumstances when it is desirable to improve clot collection. Similarly, in those circumstances where there is a concern of creating trauma on delicate blood vessels, the radially extending portions 406 may have a diameter that is smaller than the vessel diameter. It is contemplated that different sizes of the device 402 will be available for selection by the user for a particular presentation of the patient.

As for the length of the clot treatment device 402, it is known that a typical pulmonary embolism will have a length within the range between about 2 em and 10 em and sometimes between about 1 em and 20 em. Accordingly, in a preferred embodiment, the clot treatment device 402 will have a length that exceeds the length of the embolism so that a portion of the clot treatment device is positioned distal of the clot 100 during expansion.

With regard to the delivery catheter 606, in a preferred embodiment for use with a pulmonary embolism, the size will be around 1 F-6 F. Smaller diameters will pass through the clot 100 more easily. In addition, the delivery catheter 606 may have stiffness characteristics to assist in making sure the delivery catheter 606 passes through the clot in a smooth manner. Such stiffness characteristics include self expanding Nitinol wire braids or stent structures that are contained within the structure of the delivery catheter 606. The delivery catheter 606 also has sufficient flexibility so that it may carry the clot treatment device 402 and still pass through a tortuous vessel path as described above starting with insertion of the delivery catheter 606 in the femoral vein FV.

In some preferred embodiments, the method and device in accordance with the present invention may reduce the Mean Resting Pulmonary Artery Pressure (MRPAP). Upon at least partial relief from the clot 100, MRPAP may be reduced by about 20-50 mmHg to a normal range of 8-20 mmHg. In some embodiments, the reduction in MRPAP may be about 25-50%. In some embodiments, the reduction in MRPAP may be about 15% to 40% and in other embodiments between about 30% and 75%.

Such a reduction in MRPAP can occur in two steps. A first step is when the clot treatment device 402 is first deployed and blood flow is at least partially restored. A second step may be when the clot treatment device 402 is retracted and at least some of the clot 100 is removed from the vessel. A third step may be after the clot treatment device 402 has been removed and the effect of the body's own processes and/or thrombolytic drugs that may have been used before, during or after the procedure take effect upon clot that has been disrupted by the clot treatment device.

FIG. 15 is a side view of an embodiment of a guide catheter 1500 for use with any of the foregoing embodiments of the clot treatment devices 402 (not shown in FIG. 15). The guide catheter 1500 can include a shaft 1502 having a sufficiently large lumen to accommodate the delivery catheter 606 (FIGS. 4 and 5A). The guide catheter 1500 can further include an expandable guide member 1510 at the distal end of the shaft 1502 configured to expand radially outward to contact or nearly contact the vessel wall VW. The guide member can be formed from a permeable, radially expanding material, such as a mesh or other macroporous structure (e.g., a braid of wires or filaments). The guide member 1510, for example, may be formed from a tubular braid of elastic or super-elastic filaments such as Nitinol that has been heat set into the desired expanded shape. The permeable, radially expanding guide member 1510 may have advantages over an occlusive member such as a balloon or impermeable funnel. For example, the guide member 1510 allows a substantial amount of blood flow BF to continue flowing through the blood vessel where therapy is being directed. In addition, the guide member 1510 positions the shaft 1502 and delivery catheter 606 at or near the center of the vessel. The clot treatment device 402 (not shown in FIG. 15) may also be substantially self-centering upon deployment, and the guide member 1510 may further guide the clot material captured by the clot treatment device 402 into the shaft 1502 as the clot treatment device 402 moves into proximity of the distal end of the shaft 1502. This is expected to enhance aspiration of the clot material. For example, in the embodiment shown in FIG. 15, the radially expanding guide member 1510 has a funnel shape adjacent the distal end of the shaft 1502 to guide thrombus material into the distal opening of the shaft 1502 where it can be more readily aspirated.

The radially expanding guide member 1510 may also be formed by conventional machining, laser cutting, electrical discharge machining (EDM) or other means known in the art to make a fenestrated, mesh or porous structure that can be affixed near the distal end of the shaft 1502. In some embodiments the radially expanding guide member 1510 may self-expand, but in other embodiments it may be actuated by an operator using, for example, electrical or electromechanical means. By having a porous radially expanding guide member 1510, the guide catheter 1500 may be substantially centered within a vessel without blocking a large portion of the flow around the catheter. In some embodiments, the radially expanding guide member 1510 may block less than about 50% of the flow about the catheter and in other embodiments less than about 25% of the flow. When the guide member 1510 is made with a braid of filaments (e.g. wires), it may be formed from a tubular braid.

In some embodiments, the tubular braid may be formed with approximately 12 to approximately 144 filaments, or in other embodiments from about 36 to about 96 filaments. The pores as measured by the largest circle that can be inscribed within an opening of the mesh may be between about 0.5 mm and 5 mm.

FIGS. 16 and 17 show additional embodiments of guide members 1610 and 1710, respectively, that can be used instead of or in addition to the guide member 1510. Referring to FIGS. 15 and 16, one or both ends of the tubular braid of the guide members 1510 and 1610 may be inverted and attached to the catheter body. Referring to FIG. 17, neither end of the guide member 1710 is inverted. With the distal end inverted, it advantageously may form a funnel adjacent the distal opening of the catheter that may enhance clot capture and aspiration.

Figure 18:
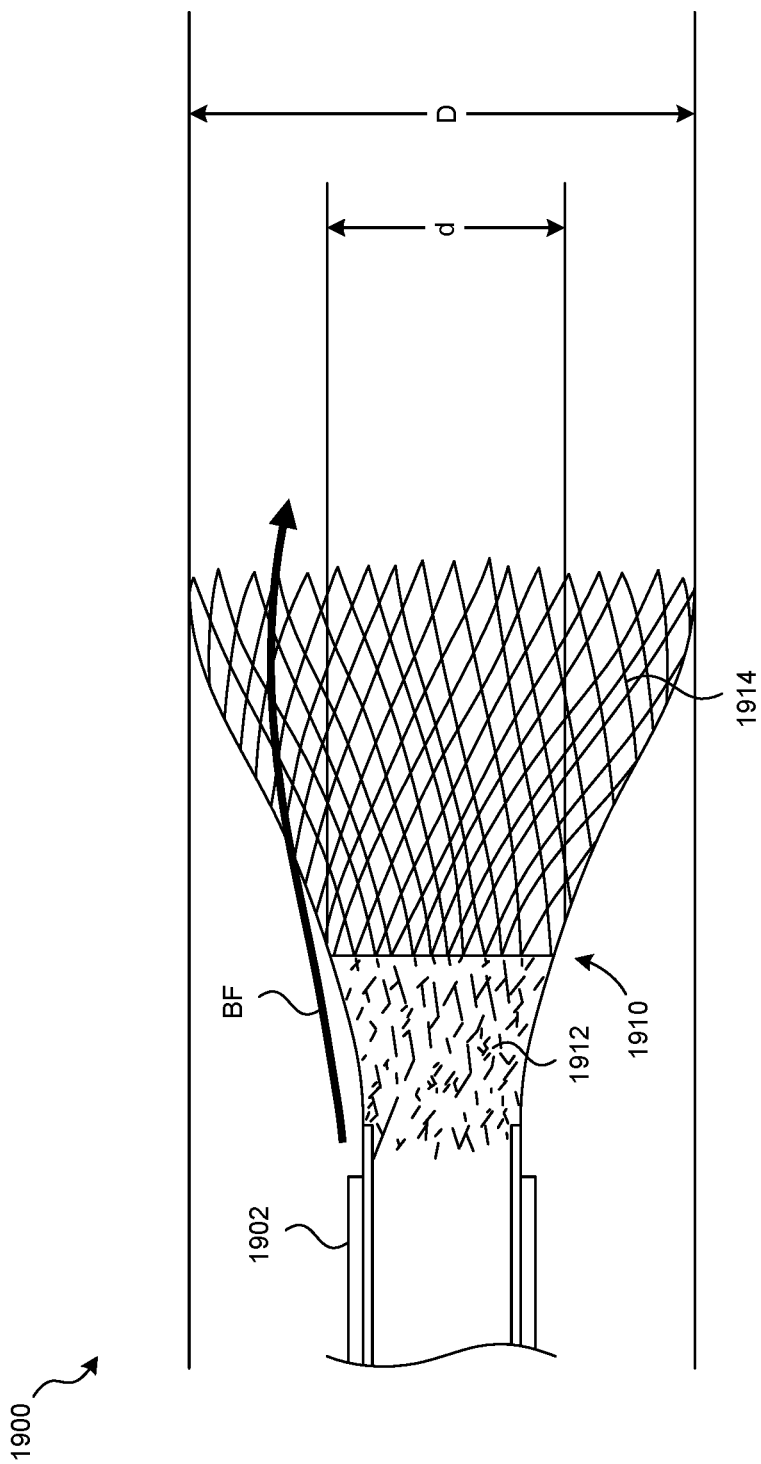

FIG. 18 shows an embodiment of a guide catheter 1900 having a shaft 1902 and a guide member 1910 in accordance with another embodiment of the technology. In the embodiment shown in FIG. 18, the guide member 1910 has a tapered or funnel shape, and includes a non-permeable portion 1912 and a permeable portion 1914. The permeable portion 1914 can comprise a flared radially expanding mesh that has, at least in part, a tapered or funnel shape, and the non-permeable portion 1912 may have a substantially non-porous or otherwise non-permeable material or coating over the mesh. Preferably, the non-permeable material is a highly elastic material such as polyurethane, silicone, latex rubber and the like so that it can flex with the expansion of the mesh. In some embodiments, the non-permeable material covers a proximal portion of the mesh as shown in FIG. 18. The non-permeable portion 1912 may divert some flow away from the distal end of the catheter. The covering may cover a portion of the mesh to a diameter "d". In some embodiments, the diameter d of the covering is less than about 75% of the diameter "D" of the mesh funnel. In some embodiments, the diameter d may be less than about 50% of diameter D. The concept of a non-permeable material can also be applied to the guide catheter 1500 shown above in FIG. 15. For example, the expandable member 1510 of the guide catheter 1500 can have a non-permeable portion 1512 at the proximal portion of the expandable guide member 1510 similar to the non-permeable portion 1912 shown and described with reference to FIG. 18.

FIGS. 19-27 show additional embodiments of clot treatment devices 402 in accordance with the present technology. The embodiments of the clot treatment devices 402 shown in FIGS. 19-27 can restore blood flow and capture clot material in a manner similar to the embodiments of the clot treatment devices 402 described above with respect to FIGS. 4-18. The embodiments of the clot treatment devices 402 related to FIGS. 19-27 can also be made from the same materials and be deployed in the same manner as described above with respect to FIGS. 4-18. As such, many of the features, materials and benefits of the clot treatment devices 402 shown in FIGS. 4-18 are applicable to the clot treatment devices shown in FIGS. 19-27.

FIG. 19 shows an embodiment of the clot treatment device 402 that includes a plurality of capture elements, such as clot engagement ("CE") members 1952. The CE members 1952 can be (a) arcuate as shown in FIG. 19, (b) bent at one or more angles (e.g., 30°, 45°, 60°, 90°, 135°, etc.), and/or (c) straight (e.g., project outward along a straight line). In some embodiments, the clot treatment device 402 can include a combination of arcuate, angled and/or straight CE members. In other embodiments, the clot treatment device 402 can include a single CE member 1952. The CE members 1952 can be interwoven into the mesh structure of the device 402 (see FIG. 21). The CE members 1952 can also be bonded, soldered, welded, tied or otherwise secured to the mesh structure or mechanically interlocked with the mesh structure. As the clot treatment device 402 is unsheathed during deployment, the CE members 1952 can radially extend and form a heat-set shape configured to penetrate and fasten the clot to the treatment device 402. The CE members 1952 can accordingly define hook-like capture elements in several embodiments of the present technology.

The CE members 1952 can be disposed about an exterior surface of the device 402. For example, as shown in FIG. 19, the CE members 1952 can be arranged in one or more circumferential rows 1954 that are evenly positioned along a longitudinal axis of the device 402. In other embodiments, the CE members 1952 can have any suitable arrangement and/or positioning about the device (e.g., arranged in a helical pattern, off-set rows, random, or irregular or otherwise uneven/non-uniform spacing, etc.).

As shown in FIG. 19, the CE members 1952 can curve proximally such that a concave portion 1956 of the CE members 1952 face a proximal region 402b of the device 402. In some embodiments, the CE members 1952 can curve distally such that a concave portion of the CE members 1952 face a distal region 402a of the device 402 (not shown). In particular embodiments, the clot treatment device 402 includes both distally-curving and proximally-curving CE members.

The CE members can have a single radius of curvature or have regions with different radii or have a complex or changing radius of curvature. For example, as shown in FIG. 20, one or more of the CE members 1952 can have a first portion 1958 that has a first radius R and a second portion 1960 (e.g., the distal region of the CE member 1952) that has a second radius r that is smaller than the first radius R. In some embodiments, the first radius R may range from about 2 mm to about 15 mm, and the second radius r may range from about 0.25 mm to about 5 mm. Additionally, the CE members 1952 can have a range of arc lengths. For example, in some embodiments the CE members 1952 can have an arc length greater than 180 degrees. In certain embodiments, the arc length can be between 180 degrees and 330 degrees.

Figure 22:
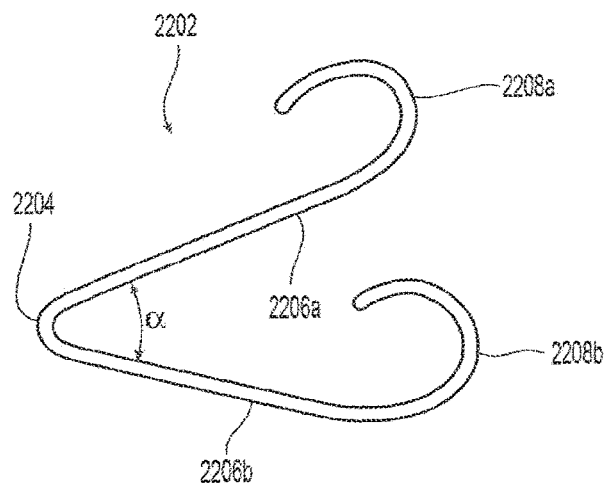
Figure 24:
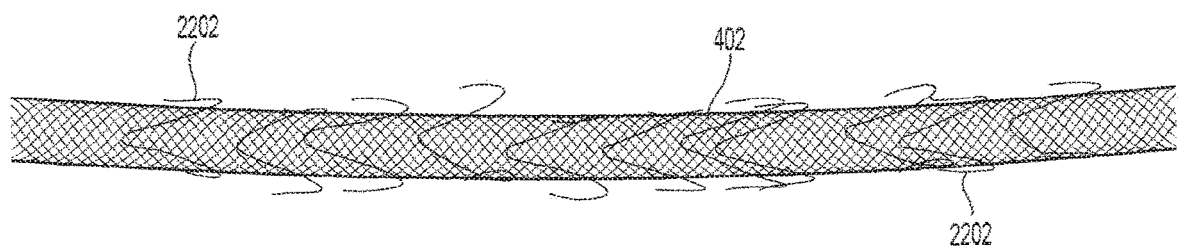
FIGS. 24-25 are side views of clot treatment devices configured in accordance with embodiments of the present technology.
Figure 25:
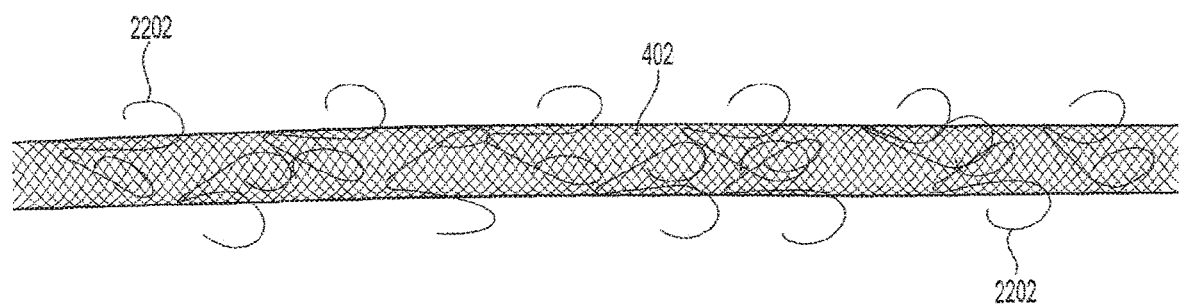

FIG. 22 shows another embodiment of a CE member 2202 having a V-shaped base 2204 that branches into a first arm 2206a and a second arm 2206b. The V-shaped base 2204 and/or any portion of the first and/or second arms 2206a, 2206b can be interwoven into the mesh structure of the clot treatment device 402, as shown in FIGS. 24 and 25. In some embodiments, the angle a between the first and second arms 2206a, 2206b may be between about 40 degrees and about 100 degrees. Although FIG. 24 shows a plurality of such CE members 2202 disposed about a clot treatment device 402, in other embodiments the device 402 can only include a single CE member 2202.

As shown in FIG. 25, the first arm 2206a and the second arm 2206b can extend into a first distal portion 2208a and a second distal portion 2208b, respectively, where the first distal portion 2208a and the second distal portion 2208b are generally arcuate. As shown in FIG. 24, in some embodiments the first distal portion 2208a and the second distal portion 2208b can be generally linear.

Figure 26:
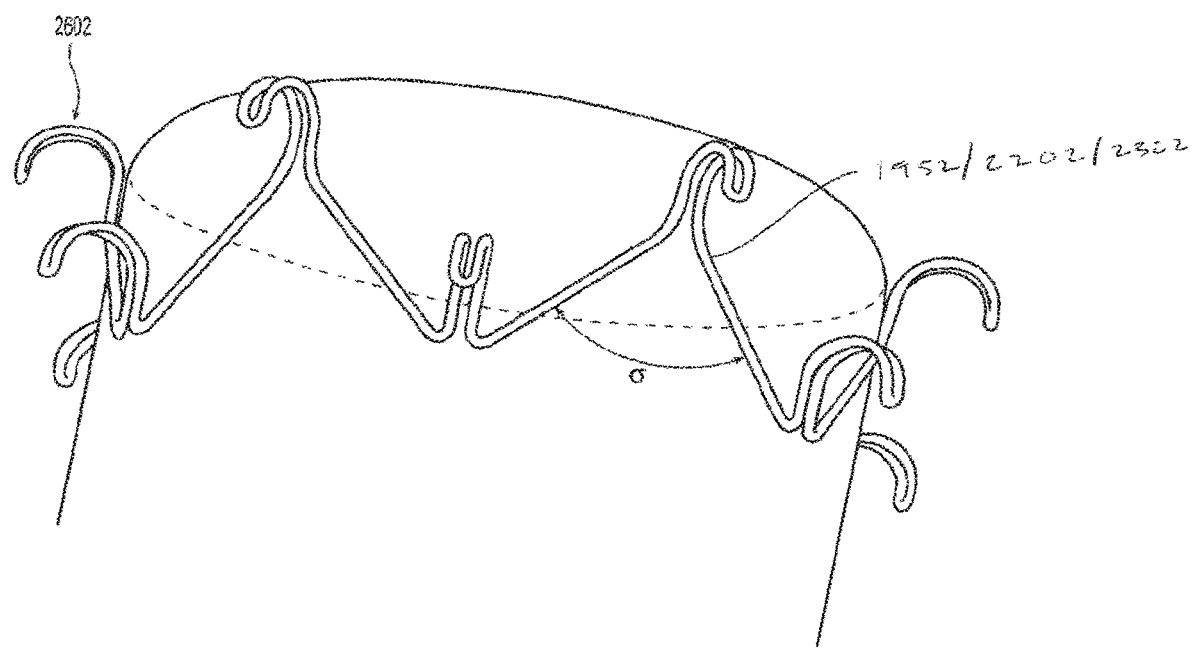
FIG. 26 is a circumferential structure including arcuate clot engagement members in accordance with embodiments of the present technology.

Referring to FIG. 26, two or more CE members can be connected to form a circumferential structure 2602 that extends around at least a portion of a circumference of a clot treatment device 402. The device 402 can include one or more circumferential structures 2602 spaced along a longitudinal axis of the device. These circumferential structures 2602 can allow for the CE members to flex with the mesh structure as it expands and contracts. In some embodiments, the angle 8 formed by the circumferential structure 2602 can be between about 40 degrees and about 100 degrees.

Figure 23:
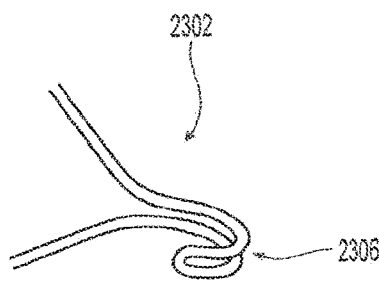
Figure 27:
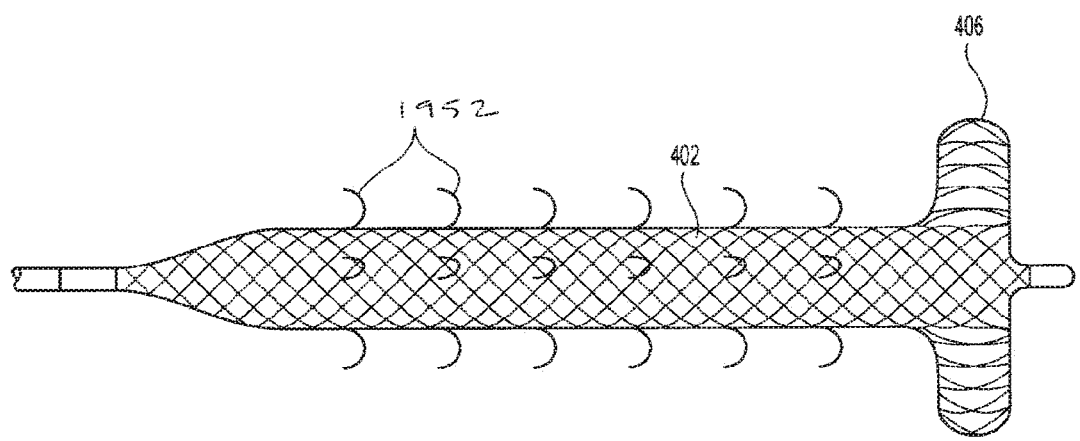
FIG. 27 is a side view of a clot treatment device having a distal radially extending member configured in accordance with another embodiment of the present technology.

FIG. 23 shows one embodiment of an CE member 2302 having a double-wire arcuate portion 2306. Referring to FIG. 27, in some embodiments, the clot treatment device 402 can include a plurality of CE member 1952 and a radially extended member 406 at a distal end. The radially extended member 406 could be a disc, balloon, screen or other clot capture member.

EXAMPLES

Several examples of the present technology are as follows:

1. A device for treating a pulmonary embolism, comprising:
   an expandable flow restoration portion; and
   a plurality of capture elements including at least a first capture element and a second capture element, wherein the flow restoration portion is between the first and second capture elements, and wherein the flow restoration portion and the capture elements are configured to move from a low-profile undeployed state sized to fit within a delivery catheter to a deployed state in which the flow restoration portion has a first cross-sectional dimension greater than that of the low-profile state such that the flow restoration portion forms a flow channel through the device and the capture elements project outwardly from the flow restoration portion.

2. The device of example 1 wherein the flow restoration portion and the capture elements comprise an expandable braided material that is heat set to have the deployed state.

3. The device of any of examples 1 and 2 wherein the flow restoration portion and the capture elements are integrally formed from a common braided material.

4. The device of any of examples 1-3, further comprising a plurality of flow restoration portions and the capture elements comprise a series of radially extending capture portions, and wherein the radially extending capture portions are separated from each other by individual flow restoration portions.

5. The device of example 4 wherein the flow restoration portions comprise expandable cylindrical sections and the capture elements comprise radially expandable disk-like capture portions of the braided material.

6. The device of example 1 wherein the flow restoration portion comprises a radially expandable cylindrical braided material and the capture elements comprise protuberances projecting from the flow restoration portion.

7. The device of any of examples 1-6 wherein the flow restoration portion has an expansion ratio from the undeployed state to the deployed state of approximately 1:4 to 1:8.

8. The device of any of examples 1-6 wherein the flow restoration portion has an expansion ratio from the undeployed state to the deployed state of approximately 1:5 to 1:7.

9. The device of any of examples 1-8 wherein the flow restoration portion has a diameter of approximately 4-8 mm in the deployed state to restore blood flow through a pulmonary embolism.

10. The device of any of examples 1-9 wherein the flow restoration portions and the capture elements comprises a self-expanding braided material, and the capture elements comprise capture portions that have a second diameter greater than the first cross-sectional dimension of the flow restoration portions in the deployed state.

11. The device of any of examples 1-3 and 6-9 wherein the flow restoration portion comprises a single expandable braided tube, and the capture elements comprise clot engagement members configured to project from the flow restoration portion in the deployed state.

12. The device of example 11 wherein the clot engagement members comprise arcuate members that form hook-like elements projecting from the flow restoration portion.

13. The device of example 11 wherein the clot engagement members are formed from wires of the expandable braided tube that defines the flow restoration portion.

14. The device of example 11 wherein the clot engagement members are formed from separate wires that project through interstices of the expandable braided tube that defines the flow restoration portion.

15. A pulmonary embolism treatment device, comprising:
   an outer elongated member having a distal end;
   an inner elongated member within the outer elongated member, wherein the inner elongated member and/or the outer elongated member slides relative to the other, and wherein the inner elongated member has a distal end; and
   an expandable member having a proximal portion attached to the distal end of the outer elongated member and a distal portion attached to the distal end of the inner elongated member, the expandable member having a flow restoration portion and a plurality of capture elements arranged along the flow restoration portion, wherein the flow restoration portion and the capture elements are configured to move from a low-profile undeployed state sized to fit within a delivery catheter to a deployed state in which the flow restoration portion has a first cross-sectional dimension greater than that of the low-profile state that defines a flow channel through the device and the capture elements project outwardly from the flow restoration portion.

16. The pulmonary embolism treatment device of example 15 wherein the expandable member comprises a braided material.

17. The pulmonary embolism treatment device of example 15 wherein the device has a plurality of flow restoration portions and the capture elements are separated by individual flow restoration portions, and wherein (a) the capture elements comprise capture portions formed from a continuous shape-memory braided material heat-set to the deployed state and (b) the capture portions project from the flow restoration portions to a second cross-sectional dimension in the deployed state.

18. The pulmonary embolism treatment device of example 17 wherein the flow restoration portions comprise cylindrical portions and the first cross-sectional dimension comprises a first diameter in the deployed state, and the capture portions comprise disk-like projections having a second diameter greater than the first diameter in the deployed state.

19. The pulmonary embolism treatment device of any of examples 11-18 wherein the flow restoration portion(s) have an expansion ratio from the undeployed state to the deployed state from 1:4 to 1:8.

20. The pulmonary embolism treatment device of any of examples 11-18 wherein the flow restoration portion(s) have an expansion ratio from the undeployed state to the deployed state from 1:5 to 1:7.

21. The pulmonary embolism treatment device of any of examples 11-20 wherein the first elongated member comprises an outer tube and the second elongated member comprises an inner tube within the outer tube.

22. The pulmonary embolism treatment device of any of examples 11-20 wherein the first elongated member comprises an outer tube and the second elongated member comprises a coil within the outer tube.

23. The pulmonary embolism device of any of examples 11-20 wherein the first elongated member comprises an outer coil and the second elongated member comprises an inner coil.

24. The pulmonary embolism treatment device of any of examples 11-23 wherein the flow restoration portion(s) and the capture elements comprise a self-expanding braided material.

25. The pulmonary embolism treatment device of any of examples 11-24 wherein the outer elongated member is configured to slide distally with respect to the inner elongated member to move the expansion member from the undeployed state to the deployed state.

26. The pulmonary embolism treatment device of any of examples 11-25, further comprising a guide catheter having a shaft with a distal end and an expandable guide member at the distal end of the shaft, wherein the shaft has a lumen configured to receive the expandable member in the undeployed state.

27. The pulmonary embolism treatment device of example 26 wherein the expandable guide member comprises radially expandable mesh.

28. The pulmonary embolism treatment device of example 27 wherein the radially expandable mesh comprises a braided material.

29. The pulmonary embolism treatment device of any of examples 26-28 wherein the expandable guide member has a funnel shape.

30. The pulmonary embolism treatment device of any of examples 26-29 wherein at least a portion of the expandable guide member is permeable to allow blood to flow through the expandable guide member when the expandable guide member is expanded.

31. The pulmonary embolism treatment device of any of examples 26-29 wherein the expandable guide member has a non-permeable portion at the distal end of the shaft and a permeable portion extending distally from the non-permeable portion.

32. A pulmonary embolism treatment device, comprising:
an elongated member having a distal end;
an expansion portion having a proximal end attached to the distal end of the elongated member, and the expansion portion having a distal end; and
an expandable member having a proximal portion attached to the distal end of the elongated member and a distal portion attached to the distal end of the expansion portion, the expandable member having at least one of flow restoration portion and a plurality of capture elements arranged such that the capture elements are separated by individual flow restoration portion, wherein the flow restoration portion and the capture elements are configured to move from a low-profile undeployed state sized to fit within a delivery catheter to a deployed state in which (a) the flow restoration portion has a first cross-sectional dimension greater than that of the low-profile state that defines a flow channel through the device and (b) the capture elements project outwardly from the flow restoration portion, and wherein the expansion portion is stretched from a normal state when the expandable member is in the undeployed state such that the expansion portion is configured to axially contract the expandable member from the undeployed state to the deployed state.

33. A method of treating a pulmonary embolism, comprising:
delivering an embolectomy device through the heart to a pulmonary embolism that at least partially restricts blood flow through a pulmonary vessel, wherein the embolectomy device has a plurality of capture elements separated by an expandable cylindrical section;
deploying the embolectomy device within the pulmonary embolism by expanding the cylindrical section into the pulmonary embolism so that the cylindrical section forms an expanded flow channel through the pulmonary embolism and thereby restores blood flow through the pulmonary embolism and by expanding the capture elements to a greater extent than the cylindrical section so that at least a portion of the pulmonary embolism is captured the capture elements;
moving the embolectomy device and at least a portion of the pulmonary embolism along the pulmonary vessel; and
withdrawing the embolectomy device and at least a portion of the pulmonary embolism from the pulmonary vessel.

34. The method of example 33 wherein deploying the embolectomy device comprises expanding a plurality of radial extendable capture elements of the embolectomy device.

35. The method of example 34, wherein at least one of the plurality of radial extendable capture elements is expanded distal relative to the pulmonary embolism.

36. The method of example 33, further comprising applying vacuum while withdrawing the embolectomy device.

37. The method of example 36, wherein withdrawing the embolectomy device includes urging the portion of the pulmonary embolism into a funnel catheter.

38. The method of example 37, wherein deploying the embolectomy device comprises expanding the device such that a surface area of the embolectomy device expands within a range of at least 200% to 400% of the surface area of a uniformly cylindrical device.

39. The method of example 33 wherein deploying the embolectomy device comprises expanding the generally cylindrical section by 400% to 800% of its diameter in the undeployed state.

40. The method according to and of examples 33-39 wherein deploying the embolectomy device comprises expanding a braided material into a preset shape having a plurality of radially extending disk-like capture portions that define the capture elements.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

We claim:

1. A system for treating a pulmonary embolism, comprising:
a clot treatment device including—
an expandable flow restoration portion; and
a plurality of capture elements including at least a first capture element and a second capture element, wherein the flow restoration portion is positioned between the first and second capture elements, and wherein the flow restoration portion and the capture elements are configured to move from a low-profile undeployed state sized to fit within a delivery catheter to a deployed state in which the flow restoration portion has a cross-sectional dimension greater than that of the undeployed state and the capture elements project outwardly from the flow restoration portion;

a guide catheter having a shaft with a distal end portion, wherein the shaft includes a lumen configured to receive the clot treatment device in the undeployed state; and an expandable guide member at the distal end portion of the shaft, wherein the expandable guide member includes a mesh having a permeable portion and a substantially non-permeable portion, wherein the non-permeable portion includes a non-permeable coating formed on a proximal portion of the mesh, and wherein the expandable guide member is configured to guide clot material into the guide catheter as the clot treatment device is withdrawn into the guide catheter.

2. The system of claim 1 wherein the permeable portion of the mesh is configured to allow blood to flow through the expandable guide member.

3. The system of claim 1 wherein the mesh is self-expanding.

4. The system of claim 1 wherein the mesh is formed from a tubular braid of elastic or super-elastic filaments that have been heat set to have a desired expanded shape.

5. The system of claim 1 wherein, when the guide catheter is positioned within a pulmonary vessel, the expandable guide member is configured to expand radially outward to contact or nearly contact the pulmonary vessel and block less than about 50% of blood flow about the guide catheter.

6. The system of claim 1 wherein the expandable guide member is configured to position the shaft at or near a center of a pulmonary vessel in which the guide catheter is positioned.

7. The system of claim 1 wherein the expandable guide member has a tapered or funnel shape for guiding thrombus material into a distal opening in the shaft.

8. The system of claim 1 wherein the substantially non-permeable portion of the mesh is affixed to the distal end portion of the shaft and the permeable portion of the mesh extends distally from the substantially non-permeable portion.

9. The system of claim 8 wherein the permeable portion has a tapered or funnel shape, and wherein the substantially non-permeable portion comprises an elastic material.

10. The system of claim 1 wherein the flow restoration portion has a first longitudinal dimension and each of the capture elements has a second longitudinal dimension, the first longitudinal dimension being greater than the second longitudinal dimension.

11. A system for treating a pulmonary embolism, comprising:
a clot treatment device including—
an outer elongated member having a distal end;
an inner elongated member within the outer elongated member, wherein the inner elongated member and the outer elongated member slide relative to each other, and wherein the inner elongated member has a distal end; and
an expandable member having a proximal portion fixed to the distal end of the outer elongated member and a distal portion fixed to the distal end of the inner elongated member, the expandable member having a flow restoration portion and a plurality of capture elements arranged along the flow restoration portion, wherein the flow restoration portion and the capture elements are configured to move from a low-profile undeployed state sized to fit within a delivery catheter to a deployed state in which the flow restoration portion has a cross-sectional dimension greater than that of the undeployed state and the capture elements project outwardly from the flow restoration portion;

a guide catheter having a shaft with a distal end portion, wherein the shaft includes a lumen configured to receive the clot treatment device in the undeployed state; and a radially expandable guide member including a mesh having a first portion affixed to the distal end portion of the shaft and a second portion extending distally from the first portion, wherein the first portion is substantially non-permeable and the second portion is permeable, wherein the first portion includes a non-permeable coating formed thereon, and wherein the guide member is configured to guide clot material into the guide catheter as the clot treatment device is withdrawn into the guide catheter.

12. The system of claim 11 wherein, when the guide member is expanded—
the guide member defines a distal opening,
the first portion has a first diameter, and
the second portion has a second diameter greater than the first diameter.

13. The system of claim 11 wherein, when the guide catheter is positioned within a pulmonary vessel and the guide member is expanded—
the first portion is configured to divert blood flow away from the distal end portion of the shaft, and
the second portion is configured to allow blood to flow through the guide member and around the guide catheter.

14. The system of claim 11 wherein the flow restoration portion has a first longitudinal dimension and each of the capture elements has a second longitudinal dimension, the first longitudinal dimension being greater than the second longitudinal dimension.

15. A system for treating a pulmonary embolism, comprising:
a clot treatment device configured to move from a low-profile undeployed state sized to fit within a delivery catheter to a deployed state, wherein the clot treatment device has a greater cross-sectional dimension in the deployed state than in the undeployed state;
a guide catheter having a shaft with a distal end, wherein the shaft includes a lumen configured to receive the clot treatment device in the undeployed state; and
an expandable guide member including a mesh having a first portion affixed at or near the distal end of the shaft and a second portion extending distally from the first portion, wherein the first portion includes a non-permeable coating formed thereon, and wherein the second portion is permeable to allow blood to flow through the expandable guide member when the expandable guide member is expanded.

16. The system of claim 15 wherein the second portion is radially expanding and has a tapered or funnel shape, and wherein the first portion comprises an elastic material configured to flex with expansion of the second portion.

* * * * *